(12) United States Patent
Littler

(10) Patent No.: US 12,577,593 B2
(45) Date of Patent: Mar. 17, 2026

(54) DHA ENRICHED POLYUNSATURATED FATTY ACID COMPOSITIONS

(71) Applicant: Nuseed Nutritional US Inc., West Sacramento, CA (US)

(72) Inventor: Stuart Littler, Clayton (AU)

(73) Assignee: Nuseed Nutritional US Inc., West Sacramento, CA (US)

( * ) Notice: Subject to any disclaimer, the term of this patent is extended or adjusted under 35 U.S.C. 154(b) by 1105 days.

(21) Appl. No.: 17/253,944

(22) PCT Filed: Dec. 20, 2018

(86) PCT No.: PCT/EP2018/086382

§ 371 (c)(1),
(2) Date: Dec. 18, 2020

(87) PCT Pub. No.: WO2019/242875

PCT Pub. Date: Dec. 26, 2019

(65) Prior Publication Data

US 2021/0254110 A1 Aug. 19, 2021

(30) Foreign Application Priority Data

Jun. 21, 2018 (EP) ..................................... 18179080

(51) Int. Cl.
*C12P 7/6472* (2022.01)
*A23D 7/00* (2006.01)
(Continued)

(52) U.S. Cl.
CPC .............. *C12P 7/6472* (2013.01); *A23D 7/00* (2013.01); *A23D 9/00* (2013.01); *A61K 31/202* (2013.01); *C12P 7/6458* (2022.01)

(58) Field of Classification Search
CPC .......... A23D 7/00; A23D 9/00; A61K 31/202; C12P 7/6472
See application file for complete search history.

(56) References Cited

U.S. PATENT DOCUMENTS

| 5,130,061 A | 7/1992 | Cornieri et al. |
| 5,237,080 A | 8/1993 | Daute et al. |
| | (Continued) | |

FOREIGN PATENT DOCUMENTS

| AU | 2017251727 A1 | 11/2017 |
| CA | 2 822 314 A1 | 7/2012 |
| | (Continued) | |

OTHER PUBLICATIONS

"Omega-3 Supplement Guide: What to Buy and Why", URL: https://www.healthline.com/nutrition/omega-3-supplement-guide, 2020, 13 pages.
(Continued)

*Primary Examiner* — Erik Kashnikow
*Assistant Examiner* — Assaf Zilbering
(74) *Attorney, Agent, or Firm* — Wiley Rein LLP

(57) ABSTRACT

There is provided a vegetable-based lipid composition comprising high levels of at least three different long-chain polyunsaturated fatty acids (typically as fatty acid esters). The compositions contain DHA as the principal long-chain polyunsaturated fatty acid. The composition is obtainable from a single source by conventional processing methods, and has improved stability properties.

17 Claims, 2 Drawing Sheets

Figure 1:
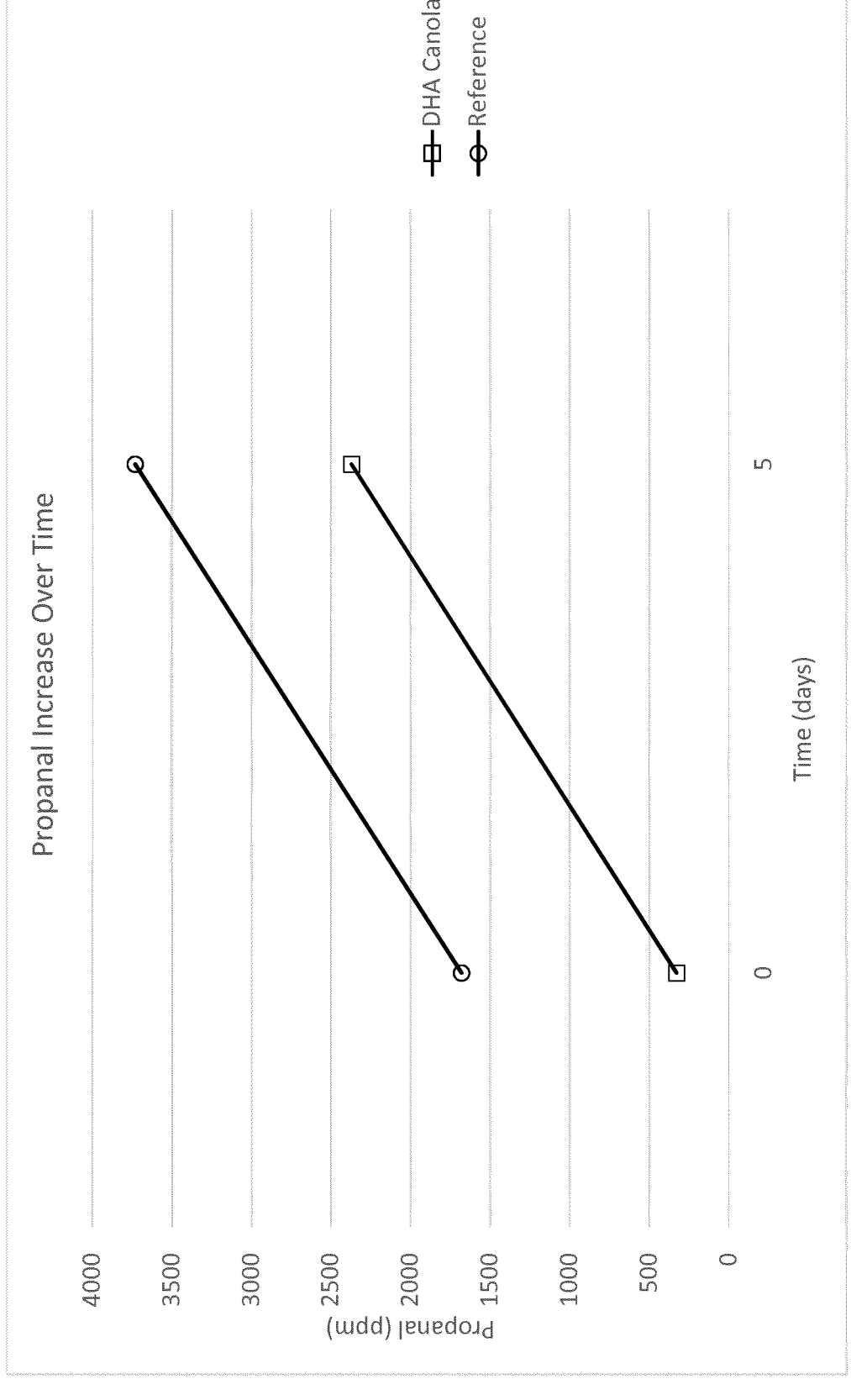

(51) Int. Cl.
A23D 9/00 (2006.01)
A61K 31/202 (2006.01)
C12P 7/6458 (2022.01)

(56) References Cited

U.S. PATENT DOCUMENTS

| | | | |
|---|---|---|---|
| 5,502,077 | A | 3/1996 | Breivik et al. |
| 5,672,726 | A | 9/1997 | Ryu et al. |
| 7,001,610 | B2 | 2/2006 | Stewart |
| 7,091,369 | B2 | 8/2006 | Smith et al. |
| 7,642,287 | B2 | 1/2010 | Guzman et al. |
| 8,062,688 | B2 | 11/2011 | Greither |
| 8,455,035 | B2 | 6/2013 | Rein et al. |
| 8,501,251 | B2 | 8/2013 | Clunies et al. |
| 8,551,551 | B2 | 10/2013 | Perlman |
| 8,586,772 | B2 | 11/2013 | Harting Glade et al. |
| 8,957,231 | B2 | 2/2015 | Sepulveda Reyes et al. |
| 9,040,730 | B2 | 5/2015 | Liang et al. |
| 9,145,533 | B2 | 9/2015 | Breivik et al. |
| 9,234,157 | B2 | 1/2016 | Kelliher et al. |
| 9,365,800 | B2 | 6/2016 | Harata et al. |
| 9,409,851 | B2 | 8/2016 | Breivik et al. |
| 9,532,963 | B2 | 1/2017 | Hustvedt et al. |
| 9,546,125 | B2 | 1/2017 | Oroskar |
| 9,556,102 | B2 | 1/2017 | Petrie et al. |
| 9,796,658 | B2 | 10/2017 | Raman et al. |
| 10,125,084 | B2 | 11/2018 | Petrie et al. |
| 2004/0209953 | A1 | 10/2004 | Wai Lee |
| 2005/0244564 | A1 | 11/2005 | Perlman |
| 2006/0039992 | A1 | 2/2006 | Miller et al. |
| 2007/0299272 | A1 | 12/2007 | Wanasundara |
| 2008/0033191 | A1 | 2/2008 | Schoerken et al. |
| 2009/0047378 | A1 | 2/2009 | Stewart |
| 2009/0057478 | A1 | 3/2009 | Conner |
| 2010/0190220 | A1 | 7/2010 | Furihata et al. |
| 2010/0227924 | A1 | 9/2010 | Cirpus et al. |
| 2010/0305347 | A1 | 12/2010 | Wanasundara |
| 2011/0027443 | A1 | 2/2011 | Mori et al. |
| 2011/0033595 | A1 | 2/2011 | Krumbholz et al. |
| 2011/0039010 | A1 | 2/2011 | Rein et al. |
| 2011/0098356 | A1* | 4/2011 | Leininger ............ A23K 20/158 |
| | | | 554/163 |
| 2011/0130458 | A1 | 6/2011 | Breivik et al. |
| 2011/0305811 | A1 | 12/2011 | Perlman |
| 2012/0027787 | A1 | 2/2012 | Minatelli et al. |
| 2012/0214771 | A1 | 8/2012 | Sampalis |
| 2012/0330043 | A1 | 12/2012 | Kelliher et al. |
| 2013/0046020 | A1 | 2/2013 | Liang et al. |
| 2013/0059768 | A1 | 3/2013 | Hallaraker et al. |
| 2013/0267597 | A1* | 10/2013 | Senanayake ............ A23L 33/30 |
| | | | 426/607 |
| 2013/0267600 | A1 | 10/2013 | Sepulveda Reyes et al. |
| 2013/0317241 | A1 | 11/2013 | Breivik et al. |
| 2013/0338387 | A1 | 12/2013 | Petrie et al. |
| 2014/0194636 | A1 | 7/2014 | Kelliher et al. |
| 2015/0159116 | A1 | 6/2015 | Patinier et al. |
| 2015/0166928 | A1 | 6/2015 | Petrie et al. |
| 2015/0203788 | A1 | 7/2015 | Petrie et al. |
| 2015/0223483 | A1 | 8/2015 | Syed et al. |
| 2015/0237886 | A1 | 8/2015 | Clunies et al. |
| 2015/0284312 | A1 | 10/2015 | Breivik et al. |
| 2016/0208296 | A1 | 7/2016 | Shimizu et al. |
| 2016/0229785 | A1 | 8/2016 | Oroskar |
| 2016/0304433 | A1 | 10/2016 | Valery et al. |
| 2017/0035719 | A1 | 2/2017 | Waibel et al. |
| 2017/0335338 | A1 | 11/2017 | Andre |
| 2018/0016590 | A1* | 1/2018 | Devine .............. C12N 15/8281 |
| 2018/0016591 | A1 | 1/2018 | Devine et al. |
| 2018/0163156 | A1 | 6/2018 | Breivik et al. |

FOREIGN PATENT DOCUMENTS

| | | | |
|---|---|---|---|
| CA | 2 718 374 | C | 5/2013 |
| CL | 2020003279 | A1 | 7/2021 |
| CL | 2020003280 | A1 | 7/2021 |
| CL | 2020003281 | A1 | 7/2021 |
| CL | 2020003282 | A1 | 7/2021 |
| CN | 1397181 | A | 2/2003 |
| CN | 1478875 | A | 3/2004 |
| CN | 1948261 | A | 4/2007 |
| CN | 101252844 | A | 8/2008 |
| CN | 101796014 | A | 8/2010 |
| CN | 101348807 | B | 7/2011 |
| CN | 103281910 | A | 9/2013 |
| CN | 103354839 | A | 10/2013 |
| CN | 103813722 | A | 5/2014 |
| CN | 103281910 | B | 4/2015 |
| CN | 104726473 | A | 6/2015 |
| CN | 104883891 | A | 9/2015 |
| CN | 103951560 | B | 12/2015 |
| CN | 103937617 | B | 4/2016 |
| CN | 103880672 | B | 5/2016 |
| CN | 104982668 | B | 8/2016 |
| CN | 103962091 | B | 1/2017 |
| CN | 106966902 | A | 7/2017 |
| CN | 105821088 | B | 7/2019 |
| CN | 112165864 | A | 1/2021 |
| DE | 39 26 658 | A1 | 2/1990 |
| EP | 0 739 591 | B1 | 6/2001 |
| EP | 1 125 914 | A | 8/2001 |
| EP | 1 529 524 | B1 | 2/2006 |
| EP | 2 675 445 | A1 | 12/2013 |
| EP | 2 509 431 | B1 | 2/2014 |
| EP | 2 172 558 | B1 | 7/2017 |
| EP | 2 443 248 | B1 | 12/2017 |
| EP | 2 713 777 | B1 | 1/2018 |
| EP | B 560 342 | A1 | 10/2019 |
| EP | 3 586 640 | A1 | 1/2020 |
| EP | 3 586 641 | A1 | 1/2020 |
| EP | 3 586 642 | A1 | 1/2020 |
| EP | 3 586 643 | A1 | 1/2020 |
| EP | 560 342 | B1 | 6/2020 |
| EP | 784 044 | A1 | 3/2021 |
| EP | 934 505 | B1 | 5/2021 |
| EP | 2 659 780 | B2 | 6/2021 |
| JP | H01207257 | A | 8/1989 |
| JP | H02289692 | A | 11/1990 |
| JP | 2819455 | B2 | 10/1998 |
| JP | 2000/104092 | A | 4/2000 |
| KR | 101761959 | B1 | 7/2017 |
| NO | 20101800 | A1 | 6/2012 |
| PL | 207036 | B1 | 10/2010 |
| WO | 1989/011521 | A1 | 11/1989 |
| WO | 94/25552 | A1 | 11/1994 |
| WO | 1996/037586 | A1 | 11/1996 |
| WO | 1996/037587 | A1 | 11/1996 |
| WO | 2005/040318 | A1 | 5/2005 |
| WO | 2005/070411 | A1 | 8/2005 |
| WO | 2006/079534 | A1 | 8/2006 |
| WO | 2007/005725 | A2 | 1/2007 |
| WO | 2007/092509 | A2 | 8/2007 |
| WO | WO2008085841 | A1 | 7/2008 |
| WO | 2009/006317 | A1 | 1/2009 |
| WO | 2010/057246 | A1 | 5/2010 |
| WO | 2010/147900 | A1 | 12/2010 |
| WO | 2011/039776 | A1 | 4/2011 |
| WO | 2011/071376 | A1 | 6/2011 |
| WO | 2012/109539 | A1 | 8/2012 |
| WO | 2012/109563 | A1 | 8/2012 |
| WO | 2012/112531 | A1 | 8/2012 |
| WO | 2012165983 | A1 | 12/2012 |
| WO | 2013013210 | A1 | 1/2013 |
| WO | 2013/039537 | A1 | 3/2013 |
| WO | 2013/103902 | A1 | 7/2013 |
| WO | 2013101559 | A1 | 7/2013 |
| WO | 2013/185184 | A2 | 12/2013 |
| WO | WO2013185184 | A3 | 12/2013 |
| WO | 2014/043053 | A1 | 3/2014 |
| WO | 2014/089274 | A1 | 6/2014 |
| WO | 2014089501 | A1 | 6/2014 |
| WO | WO2014105576 | A1 | 7/2014 |
| WO | 2014135529 | A1 | 9/2014 |
| WO | 2015/029364 | A1 | 3/2015 |
| WO | 2015/089587 | A1 | 6/2015 |

(56)                    References Cited

FOREIGN PATENT DOCUMENTS

| WO | 2015/090394 | A1 | 6/2015 |
|----|-------------|-----|--------|
| WO | 2015/196250 | A1 | 12/2015 |
| WO | 2016/102323 | A1 | 6/2016 |
| WO | 2016150936 | A1 | 9/2016 |
| WO | WO2016182452 | A1 | 11/2016 |
| WO | 2015083806 | A1 | 3/2017 |
| WO | 2017094804 | A1 | 6/2017 |
| WO | 2017/218969 | A1 | 12/2017 |
| WO | WO2017219006 | A1 | 12/2017 |
| WO | 2018/033899 | A1 | 2/2018 |
| WO | 2019/206443 | A1 | 10/2019 |
| WO | 2019/242872 | A1 | 12/2019 |
| WO | 2019/242873 | A1 | 12/2019 |
| WO | 2019/242874 | A1 | 12/2019 |
| WO | 2019/242875 | A1 | 12/2019 |

OTHER PUBLICATIONS amazon.com "Nature Made Triple Omega 3 6 9 - Fish, Flaxseed, Safflower & Olive Oils", URL: https://www.amazon.com/Nature-Made-Triple-Omega-Safflower/dp/B001ECX38Y, 7 pages.

Barceló-Coblijn, et al. "Flaxseed Oil and Fish-Oil Capsule Consumption Alters Human Red Blood Cell n-3 Fatty Acid Composition: a Multiple-Dosing Trial Comparing 2 Sources of n-3 Fatty Acid", The American Journal of Clinical Nutrition, vol. 88, Issue 3, 2008, pp. 801-809.

Chakraborty, et al. "Long Chain n-3 Polyunsaturated Fatty Acid Enriched Oil Emulsion from Sardine Oil", Marine Fisheries Information Service, T & E Ser., No. 223 & 224, 2015, pp. 3-8.

Chen, et al. "Polyunsaturated Fatty Acid Concentrates from Borage and Linseed Oil Fatty Acids", JAOCS, vol. 78, No. 5, 2001, pp. 485-488.

Choi, One-Kyun, "Separation and Purification of Eicosapentaenoic Acid and Docosahexaenoic Acid from Fish Oil", Thesis for the Degree of Master, Department of Food Technology, Kyung Hee University, Jul. 1990.

Extended European Search Report issued in European Application No. 18169368.0, mailed on Jul. 19, 2018, 8 pages.

First Examination Report received for Taiwan Patent Application No. 107146461, mailed on Oct. 30, 2019, 13 pages (6 pages of English Translation and 7 pages of Official Copy Only).

First Examination Report received for Taiwan Patent Application No. 107146464, mailed on Oct. 15, 2019, 16 pages (8 pages of English Translation and 8 pages of Official Copy).

First Office Action Received for Taiwanese Patent Application No. 107146467, mailed on Oct. 14, 2019, 23 pages '8 pages of English Translation and 15 pages of Official Copy Only).

Frank D. Gunstone, "Structured and Modified Lipids", 2001, p. 330-343.

Gu, et al. "Concentration of a-Linoleic Acid of Perilla Oil by Gradient Cooling Urea Inclusion", Agricultural Sciences in China, vol. 8, No. 6, pp. 685-690.

Guil-Guerrero, et al. "Isolation of Some PUFA from Edible Oils by Argentated Silica Gel Chromatography", Grasas & Aceites, vol. 54, 2003, pp. 116-121.

Guo, et al. "Decomposition Characteristics of Hydrogen Peroxide in Sodium Hydroxide Solution", Advanced Materials Research, vol. 610, No. 613, 2012, pp. 359-362.

Ancu, et al. "Advanced High Vacuum Techniques for w-3 Polyunsaturated Fatty Acids Esters Concentration", Revista de Chimie, vol. 66, No. 6, 2015, pp. 911-917.

Feduba, et al. "Chemoenzymatic Method for Producing Stearidonic Acid Concentrates from Stearidonic Acid Soybean Oil", Journal of the American Oil Chemists' Society, vol. 90, 2013, pp. 1011-1022.

International Search Report and Written Opinion issued in International Application No. PCT/EP2018/086369, mailed on Jan. 22, 2019, 9 pages.

International Search Report and Written Opinion received for PCT Patent Application No. PCT/EP2018/086368, mailed on Jan. 25, 2019, 9 pages.

International Search Report and Written Opinion received for PCT Patent Application No. PCT/EP2018/086375, mailed on Feb. 15, 2019, 9 pages.

International Search Report and Written Opinion received for PCT Patent Application No. PCT/EP2018/086379, mailed on Jan. 25, 2019, 9 pages.

Rimescu, et al. "Two-Step Enzymatic Synthesis of Docosahexaenoic Acid-Rich Symmetrically Structured Triacylglycerols via 2-Monoacylglycerols", JAOCS, vol. 78, No. 7, 2001, pp. 743-748.

Kun-Tsung, Lu "The Development of Vegetable Oil-Based 14 Environment-Friendly Wood Coatings", Forestry Research Newsletter, vol. 22 No. 4, pp. 28-33.

Martinez, Jose L. "Supercritical Fluid Extraction of Nutraceuticals and Bioactive Compounds", CRC Press, 2007, p. 168-181.

Miller, et al. "Dietary Supplementation with Ethyl Ester Concentrates of Fish Oil (n-3) and Borage Oil (n-6) Polyunsaturated Fatty Acids Induces Epidermal Generation of Local Putative Anti-Inflammatory Metabolites", The Journal of Investigative Dermatology, vol. 96, No. 1, 1991, pp. 98-103.

Miranda Andreia Manuela Martins, "Novel processes for extraction and fractionation of fatty acids from microbial cell mass", Department of Chemical Engineering, Thesis, 2014, pp. 232.

Murphy, et al. "Fatty Acid and Sterol Composition of Frozen and Freeze-Dried New Zealand Green Lipped Mussel (Perna canaliculus) from Three Sites in New Zealand", Asia Pacific Journal of Clinical Nutrition, vol. 12, No. 1, 2003, pp. 50-60.

Nichols, et al. "A Journey from Marine Genes to New Sustainable Land Plant Sources of Long-Chain Omega-3 oils", Marine and Atmospheric Research, 2013, 34 pages.

Nuez-Ortín, et al. "Preliminary Validation of a High Docosahexaenoic Acid (DHA) and -Linolenic Acid (ALA) Dietary Dil Blend: Tissue Fatty Acid Composition and Liver Proteome Response in Atlantic Salmon (Salmo salar) Smolts", Plos One, vol. 11, No. 8, e0161513, 2016, pp. 1-27.

Office Action received for Taiwan Patent Application No. 107146463, mailed on Feb. 11, 2020, 9 pages (5 pages of Official Copy and 4 pages of English Translation).

Rajan, et al. "Enrichment of w-3 Fatty Acids in Flax Seed Oil by Alkaline Lipase of Aspergillus Fumigatus MTCC 9657", International Journal of Food Science & Technology, 2013, vol. 49, 2013, pp. 1337-1343.

Romero, et al. "Maximizing Content of Omega-3 (EPA and DHA) in the Process of Enzymatic Acidolysis of Canola Oil and Concentrated of Long-Chain Polyunsaturated Fatty Acids (LCPUFA) in Supercritical CO2 conditions", Scientia Agropecuaria, vol. 6, No. 4, 2015, pp. 313-323.

Rupani, et al. "Lipase-Mediated Hydrolysis of Flax Seed Oil for Selective Enrichment of a-Linolenic Acid", European Journal of Lipid Science and Technology, vol. 114, 2012, pp. 1246-1253.

Spahis, et al. "Lipid Profile, Fatty Acid Composition and Pro- And Anti-Oxidant Status in Pediatric Patients with Attention-Deficit/Hyperactivity Disorder", Prostaglandins, Leukotrienes & Essential Fatty Acids, vol. 79, No. 1-2, Jul. 1, 2008, pp. 47-53.

Taylor, et al. "Fatty Acid Composition of New Zealand Green-Lipped Mussels, Perna Canaliculus: Implications for Harvesting for n-3 Extracts", Aquaculture, vol. 261, No. 1, 2006, pp. 430-439.

Tengku-Rozaina, et al. "Enrichment of Omega-3 Fatty Acids of Refined Hoki Oil", Journal of the American Oil Chemists' Society, vol. 90, 2013, pp. 1111-1119.

Thammapat, et al. "Concentration of Eicosapentaenoic Acid (EPA) and Docosahexaenoic acid (DHA) of Asian Catfish Oil by Urea Complexation: Optimization of Reaction Conditions", Songklanakarin Journal of Science and Technology, vol. 38, No. 2, 2016, pp. 163-170.

Wang, et al. "Enrichment Process for a-Linolenic Acid from Silkworm Pupae Oil", European Journal of Lipid Science and Technology, 2013, pp. 791-799.

Zuta, et al. "Concentrating PUFA from Mackerel Processing Waste", JAOCS, vol. 80, No. 9, 2003, pp. 933-936.

(56)                     References Cited

OTHER PUBLICATIONS

Extended European Search Report issued in European Application No. 18179072.6, mailed on Jan. 3, 2019, 7 pages.
Meng, J., Jiang, Y. & Tao, J. Fatty acid composition and PIFADs expression related to α-linolenic acid biosynthesis in herbaceous peony (Paeonia lactiflora Pall.). Acta Physiol Plant 39, 222 (2017).
Latyshev N. et al., European Journal of Lipid Science and Technology. 2014, 116. pp. 1608-1613.
Notice of Rejection mailed Jul. 12, 2023 for Japanese Patent Application No. 2020-571371.
Official Communication mailed Jun. 26, 2023 for Columbian Patent Application No. NC2021/0000418.
Adkins Yuriko, et al. "Dietary Docosahexaenoic Acid andtrans-10, cis-12-Conjugated Linoleic Acid Differentially Alter Oylipin Profiles in Mouse Periuterine Adiopose Tissue", Lipids, Springer, DE, vol. 52, No. 5, Apr. 13, 2017, pp. 399-413, XPO36233589, ISSN:

0024-4201, DOI: 10.1007/S11745-017-4252-3 [retrieved on Apr. 13, 2017] the whole documente document.
International Search Report of PCT Appln. No. PCT/EP2018/086382, dated Jan. 31, 2019.
PCT International Preliminary Report on Patentability of PCT Appln. No. PCT/EP2018/086382 dated Dec. 22, 2020.
Office Action received for Chilean Patent Application No. 202003281, mailed on Jun. 16, 2022, 17 pages (official copy only).
Office Action received for Chilean Patent Application No. 202003282, mailed on Jun. 16, 2022, 16 pages (official copy only).
Sudibyo, et al. Defect and Diffusion Forum Bio-Synthesis of Eicosapentaenoic Acid (EPA) from Palm Oil Effluent Using Anaerobic Process.
Garcia Solaesa et al., "Production and concentration of monoacylglycerols rich in omega-3 polyunsaturated fatty acids by enzymatic glycerolysis and molecular distillation", Food Chemistry, 190, pp. 960-967, https://doi.org/10.1016/j.foodchem.2015.06.061, Jan. 1, 2016 (Jan. 1, 2016).

* cited by examiner

DHA ENRICHED POLYUNSATURATED FATTY ACID COMPOSITIONS

RELATED APPLICATIONS

This Application is a § 371 National Stage Application of PCT/EP2018/086382, filed Dec. 20, 2018, which claims priority benefit of Application No. EP 18179080.9, filed Jun. 21, 2018, each of which are incorporated entirely herein by reference for all purposes.

FIELD OF THE INVENTION

The embodiments disclosed herein relate to new lipid compositions that are enriched with multiple polyunsaturated fatty acids. The polyunsaturated fatty acid compositions have a number of health benefits, including nutritional benefits, and are potentially obtainable from a single source that is both scalable and sustainable. They also have an enhanced stability to oxidation.

BACKGROUND

Omega-3 long chain polyunsaturated fatty acids (LC-PUFAs) are widely recognised as important compounds for human and animal health. These fatty acids may be obtained from dietary sources or to a lesser extent by conversion of linoleic (LA, 18:20-6) or α-linolenic (ALA, 18:3ω-3) fatty acids, all of which are regarded as essential fatty acids in the human diet.

From a nutritional standpoint, the most important omega-3 fatty acids are probably α-linolenic acid, eicosapentaenoic acid ("EPA"; 20:5n-3), and docosahexaenoic acid ("DHA"; 22:6n-3). DHA is a LC-PUFA, which is important for brain and eye development. Ingestion of omega-3 PUFAs may also help to prevent coronary diseases. Medical studies clearly indicate that these fatty acids have beneficial health aspects, such as improved cardiovascular and immune functions and reduction of cancer, diabetes, and high blood pressure. Clinical results have demonstrated that a dietary intake of 5.5 g of omega-3 PUFAs per week may be linked to a 50% reduction in the risk of primary cardiac arrest. Consequently, oil containing omega-3 PUFAs has been in high demand for pharmaceutical and dietetic purposes.

Generally, the oxidative stability of a fatty acid decreases noticeably as the number of carbon-carbon double bonds, or the degree of unsaturation, increases. Unfortunately, ALA, EPA, and DHA are all polyunsaturated fats that tend to oxidise readily. EPA (with 5 carbon-carbon double bonds) is significantly more prone to oxidation than ALA; DHA (with 6 carbon-carbon double bonds) is even more prone to oxidation than EPA. As consequence, increasing the omega-3 content tends to reduce the shelf life of many products. These problems become particularly acute with, oils including significant amounts of EPA or DHA.

US 2015/223483 discloses canola oil-based blends which have improved oxidative stability. The stability is achieved by the addition of one or more additives.

US 2011/0027443 discloses fat and oil compositions containing particular blends of oleic acid, linoleic acid, alpha linolenic acid and LC-PUFAs with an improved flavour profile. US 2004/209953 discloses nutritional products containing predominantly monoglycerides and diglycerides of LC-PUFAs. U.S. Pat. No. 5,130,061 describes the use of transesterification and distillation processes to extract DHA from crude oils. U.S. Pat. No. 9,040,730 describes the purification of lipid mixtures containing PUFAs in order to reduce the quantity of undesired sterols in the composition. In each of these cases, fish or microbial oils are used as the source material from which specific blends are obtained.

International patent application no. WO 2013/185184 discloses processes for producing ethyl esters of polyunsaturated fatty acids.

International patent application no. WO 2015/089587 and US patent application no. US 2015/0166928 discloses plant lipid compositions comprising a mixture of omega-3 and omega-6 fatty acids. Genetically modified canola is described in WO 2017/218969 and WO 2017/219006.

International patent application nos. WO 2016/182452 and WO 2014/105576 disclose compositions containing significant quantities of DHA and EPA.

The listing or discussion of an apparently prior-published document in this specification should not necessarily be taken as an acknowledgement that the document is part of the state of the art or is common general knowledge.

DISCLOSURE OF THE INVENTION

According to a first aspect of the invention, there is provided a vegetable-based lipid composition comprising:
   (i) docosahexaenoic acid (22:6n-3) in an amount of from about 50% to about 85% by weight of the total fatty acid content of the composition;
   (ii) a second polyunsaturated fatty acid in an amount of from about 10% to about 90% by weight of the docosahexaenoic acid; and
   (iii) a third polyunsaturated fatty acid in an amount of from about 10% to about 70% by weight of the second polyunsaturated fatty acid;
wherein the total amount of all other fatty acids in the composition is up to about 20% by weight of the total fatty acid content of the composition, and wherein each of the docosahexaenoic acid, and the second and third polyunsaturated fatty acids is independently provided independently in the form of a fatty acid, a fatty acid salt, a fatty acid ester or a salt of a fatty acid ester; wherein the amount of EPA in the composition is less than 10% by weight of the amount of DHA.

Said lipid compositions are referred to herein as the "compositions of the invention".

The present invention relates to lipid compositions containing high levels of a first polyunsaturated fatty acid (DHA), together with at least two other polyunsaturated fatty acids, each of which may be in the form of a free fatty acid, a salt, an ester or a salt of an ester. These compositions have been found to be obtainable from sustainable sources, such as plant sources. They have also been found to have an improved storage stability profile which is evidenced by a reduction in degradation by oxidation during storage. Many polyunsaturated fatty acids, including DHA in particular, are recognised as important compounds for human and animal health. These compositions can be used in feedstuffs, nutraceuticals, cosmetics and other chemical compositions, and they may be useful as intermediates and active pharmaceutical ingredients.

Fatty acid levels in the compositions of the invention can be determined using routine methods known to those skilled in the art. Such methods include gas chromatography (GC) in conjunction with reference standards, e.g. according to the methods disclosed in the examples. In a particular method, the fatty acids are converted to methyl or ethyl esters before GC analysis. Such techniques are described in the Examples. The peak position in the chromatogram may be used to identify each particular fatty acid, and the area under each peak integrated to determine the amount. As used herein, unless stated to the contrary, the percentage of particular fatty acid in a sample is determined by calculating the area under the curve in the chromatogram for that fatty acid as a percentage of the total area for fatty acids in the chromatogram. This corresponds essentially to a weight percentage (w/w). The identity of fatty acids may be confirmed by GC-MS.

The term "polyunsaturated fatty acid", or alternatively "PUFA", refers to a fatty acid which comprises at least two carbon-carbon double bonds. The terms "long-chain polyunsaturated fatty acid" and "LC-PUFA" refer to a fatty acid which comprises at least 20 carbon atoms and at least two carbon-carbon double bonds in its carbon chain, and hence include VLC-PUFAs. As used herein, the terms "very long-chain polyunsaturated fatty acid" and "VLC-PUFA" refer to a fatty acid which comprises at least 22 carbon atoms and at least three carbon-carbon double bonds in its carbon chain. Ordinarily, the number of carbon atoms in the carbon chain of the fatty acid refers to an unbranched carbon chain. If the carbon chain is branched, the number of carbon atoms excludes those in sidegroups.

Long-chain polyunsaturated fatty acids may be ω3 ("omega-3") fatty acids, that is, fatty acids having a desaturation (carbon-carbon double bond) in the third carbon-carbon bond from the methyl end of the fatty acid. They may alternatively be ω6 ("omega-6") fatty acids, that is, fatty acids having a desaturation (carbon-carbon double bond) in the sixth carbon-carbon bond from the methyl end of the fatty acid. Whilst other unsaturation patterns may be present, the ω6 and particularly ω3 forms are particularly relevant in the context of the present invention.

The compositions of the invention comprise at least three different polyunsaturated fatty acids. The first polyunsaturated fatty acid (DHA) is the most abundant fatty acid present in the composition (by weight relative to the total fatty acid content of the composition).

References to docosahexaenoic acid and "DHA" in this context are, unless otherwise specified, references to the ω3 form of docosahexaenoic acid, that is docosahexaenoic acid having a desaturation (carbon-carbon double bond) in the third carbon-carbon bond from the methyl end of the fatty acid. Shorthand forms that may be used interchangeably include "22:6n-3" and "22:6ω-3".

The DHA and the second and third PUFAs may each independently be present in the form of a fatty acid, a fatty acid salt, a fatty acid ester or a salt of a fatty acid ester.

As used herein, the term "fatty acid" refers to a carboxylic acid (or organic acid), often with a long aliphatic tail, either saturated or unsaturated. Typically, fatty acids have a carbon-carbon bonded chain of at least 8 carbon atoms in length, more particularly at least 12 carbons in length. Most naturally occurring fatty acids have an even number of carbon atoms because their biosynthesis involves acetate which has two carbon atoms. The fatty acids may be in a free state (non-esterified), referred to herein as a "free fatty acid", or in an esterified form such as an alkyl ester, part of a triglyceride, part of a diacylglyceride, part of a monoacylglyceride, acyl-CoA (thio-ester) bound or other bound form, or a mixture thereof. The fatty acid may be esterified as a phospholipid such as a phosphatidylcholine, phosphatidylethanolamine, phosphatidylserine, phosphatidylglycerol, phosphatidylinositol or diphosphatidylglycerol forms, though preferably it is esterified as an alkyl ester, especially as an ethyl ester. For the avoidance of doubt, unless otherwise stated, the term "fatty acid" encompasses free fatty acids, fatty acid esters and salts of either of these. Unless otherwise stated, quantitative values associated with particular fatty acids refer to the amount (calculated based on weight) of that fatty acid that is present, irrespective of the form (e.g. free acid or ester) in which it is present.

Each fatty acid in the composition may also be provided in the form of a salt of a fatty acid, for example an alkali salt or alkaline earth salt. Particular salts that may be mentioned include lithium salts and calcium salts. Such salts have potential additional medicinal benefits or offer processability improvements. Similarly, a fatty acid ester may be provided in the form of a salt of a fatty acid ester. Any combination of fatty acids in the form of free fatty acids, salts, esters or salts of esters may be present in compositions of the invention. By this, we mean that, for the sake of example, the DHA may be present predominantly as an ethyl ester, the second PUFA may be present predominantly as a calcium salt of a methyl ester, and the third PUFA may be present predominantly as a free fatty acid.

"Saturated fatty acids" do not contain any double bonds or other functional groups along the chain. The term "saturated" refers to hydrogen, in that all carbons (apart from the carboxylic acid [—COOH] group) contain as many hydrogens as possible. In other words, the omega (ω) end is attached to three hydrogen atoms ($CH_3$—) and each carbon within the chain is attached to two hydrogen atoms (—$CH_2$—). The term "total fatty acid" includes fatty acids in all forms, be they saturated or unsaturated, free acids, esters and/or salts.

The term "about," as used herein when referring to a measurable value such as an amount of a compound, weight, time, temperature, and the like, refers to variations of 20%, 10%, 5%, 1%, 0.5%, or even 0.1% of the specified amount.

Compositions of the invention that may be mentioned include those that contain a high concentration of omega-3 fatty acids, many of which are so-called "essential fats" that are considered to be particularly important for human health. Omega-3 fatty acids can have beneficial effects on HDL cholesterol levels, support brain development in the young, and have been shown to benefit mental health. These fatty acids are generally considered to be precursors to eicosanoids with anti-inflammatory properties. Particular compositions of the invention that may be mentioned include those in which the total amount of omega-3 polyunsaturated fatty acids in the lipid composition is at least about 80%, such as at least about 85%, by weight of the total fatty acid content of the composition.

Omega-6 fatty acids are also considered to be important for human health. In particular, certain omega-6 fatty acids are "essential fats" necessary for good health but the body is unable to synthesise them. However, omega-6 fats have been shown to be precursors to eicosanoids with more pro-inflammatory properties, and so when too many of these eicosanoids are produced, they can increase inflammation and inflammatory disease. Thus, it may be desirable to minimise the amount of such fatty acids in lipid compositions. It is generally accepted that the ratio of omega-6 to omega-3 fatty acids in the diet should be 4:1 or less. However, the normal western diet typically contains a higher proportion of omega-6 fatty acids. The lipid compositions of the present invention advantageously contain low amounts of omega-6 fatty acids, whilst simultaneously containing high amounts of the more beneficial omega-3 fatty acids. In one embodiment, the total amount of omega-6 polyunsaturated fatty acids in the composition is at most about 10% by weight of the total fatty acid content of the composition. In another embodiment, the ratio of the total weight of omega-3 polyunsaturated fatty acids to the total weight of omega-6 polyunsaturated fatty acids in the composition is at least about 10:1. In a further embodiment, the ratio of the total weight of omega-3 polyunsaturated fatty acids to the total weight of omega-6 polyunsaturated fatty acids in the composition is at least about 20:1.

Lipid compositions containing long chain polyunsaturated fatty acids are typically obtained from marine sources (e.g. fish, crustacea), algal sources, or plant sources (e.g. flax or echium). The starting organic matter is first processed in order to extract the oil (generally referred to as the "crude" oil) contained therein. In the case of plant seeds, for example, the seeds are crushed to release the oil which is then separated from the solid matter by filtration and/or decanting. The crude oils often contain levels of polyunsaturated fatty acids which are too low to be useful (e.g. as nutritional products), so enrichment is required. Where the crude oil is lacking in one or more essential components, it is often common to blend together crude or enriched oils from multiple sources (e.g. from fish and algae) to obtain the desired composition. Alternatively, enrichment may be achieved by processing the crude oil to remove unwanted components (e.g. components which deleteriously affect the product's colour, odour or stability, or unwanted fatty acids), whilst maximising the levels of the desired fatty acid components.

The compositions of the present invention are advantageously obtainable from a single source. The use of a single source facilitates efficient and economic processing of the crude oil and manufacture of the lipid compositions of the invention. By the phrase "obtainable from a single source" (or "obtained from a single source"), we mean that the lipid composition is obtainable from one or more organisms of a single taxonomic class. In a particular embodiment, the lipid composition is not derived from multiple organisms across different taxonomic classes. For example, the lipid compositions may not be blends of oils obtained from a combination of fish and algae, or a combination of fish and plants. Instead, the lipid compositions of the invention (or the "crude" oils from which the compositions can be obtained by enrichment techniques, such as transesterification, distillation and chromatography) are obtainable from a single population of organisms, for example, a single source of plant matter or vegetation. For the avoidance of doubt, the phrase "obtainable from a single source" does not exclude the use of multiple organisms of the same species as a source of the lipid composition or "crude" oil, i.e. the use of multiple fish, algal stocks, plants, or plant seeds that are of the same species. Said multiple organisms are preferably all of the same species, or from the same breeding line, or of the same plant variety, or of the same production stock or batch.

In the compositions of the invention, DHA is present in an amount of from about 50 to about 85% by weight of the total fatty acid content of the composition. In one embodiment, the DHA is present in an amount that is at least about 55% (such as at least about 60%) by weight of the total fatty acid content of the composition. In a further embodiment of the invention, the DHA is present in an amount of up to about 80% (such as up to about 75%) by weight of the total fatty acid content of the composition.

The lipid compositions of the invention advantageously have a high level of DHA relative to the amount of EPA present. Therefore, in one embodiment, the weight ratio of docosahexaenoic acid to eicosapentaenoic acid in the lipid compositions is at least about 10:1. In further embodiments, the weight ratio of docosahexaenoic acid to eicosapentaenoic acid in the lipid compositions may be at least about 20:1, such as greater than about 30:1.

Favourably, the amount of EPA in the compositions may be very low. In particular embodiments, the lipid compositions contain up to about 3%, more particularly up to about 2%, EPA by weight of the total fatty acid content of the composition.

The second polyunsaturated fatty acid may be any polyunsaturated fatty acid disclosed herein, except that the second and third PUFAs are different and neither is DHA. In one embodiment, said second polyunsaturated fatty acid is a C18-24 omega-3 polyunsaturated fatty acid containing at least 3 (e.g. at least 4) unsaturations. Particular such PUFAs that may be mentioned include α-linolenic acid ("ALA"; 18:3n-3), eicosatetraenoic acid ("ETA"; 20:4n-3), docosapentaenoic acid ("DPA"; 22:5n-3), and stearadonic acid ("SDA"; 18:4n-3). In a yet further embodiment, the second polyunsaturated fatty acid is ALA, ETA or DPA.

The compositions of the invention contain a second polyunsaturated fatty acid in an amount of from about 10% to about 90% by weight of the DHA. In an embodiment, said second polyunsaturated fatty acid is the second most abundant polyunsaturated fatty acid in the composition. In another embodiment, the second polyunsaturated fatty acid is present in an amount of from about 10% to about 60% by weight of the DHA.

The third polyunsaturated fatty acid may be any polyunsaturated fatty acid disclosed herein, except that the second and third PUFAs are different and neither is DHA. In one embodiment, said third polyunsaturated fatty acid is a C18-24 omega-3 polyunsaturated fatty acid containing at least 3 (e.g. at least 4) unsaturations. Particular such PUFAs that may be mentioned include ALA, EPA, ETA, DPA, and SDA. In a yet further embodiment, the third polyunsaturated fatty acid is ETA, EPA or DPA.

The compositions of the invention contain a third polyunsaturated fatty acid in an amount of from about 10% to about 70% by weight of the second PUFA. In an embodiment, said third polyunsaturated fatty acid is the third most abundant polyunsaturated fatty acid in the composition. In another embodiment, the third polyunsaturated fatty acid is present in an amount of from about 10% to about 65% by weight of the second PUFA.

The compositions of the invention may also contain other polyunsaturated fatty acids (i.e. in addition to DHA and the second and third PUFAs). Such additional polyunsaturated fatty acids include those described above in respect of the third PUFA (e.g. ALA, EPA, ETA, DPA, and/or SDA), as well as others such as linoleic acid ("LA"; 18:2n-6) and γ-linolenic acid ("GLA"; 18:3n-6). In the compositions of the invention the total amount of all other fatty acids in the composition is up to about 20% by weight of the total fatty acid content of the composition. By this, it is meant that the total amount of all fatty acids in the composition, not including the DHA and the second and third PUFAs, is about 20% by weight of the total fatty acid content of the composition. In a particular embodiment, the total amount of all other fatty acids in the composition is up to about 18% (e.g. up to about 16%) by weight of the total fatty acid content of the composition.

The compositions of the invention contain up to about 0.5% palmitic acid (16:0) by weight of the total fatty acid content of the composition. In particular embodiments, the compositions contain up to about 0.1%, more particularly up to about 0.05%, palmitic acid by weight of the total fatty acid content of the composition.

Preferences and options for a given aspect, feature or embodiment of the invention should, unless the context indicates otherwise, be regarded as having been disclosed in combination with any and all preferences and options for all other aspects, features and embodiments of the invention. For example, the particular quantities of DHA and the second and third PUFAs indicated in the preceding passages are disclosed in all combinations.

A particular lipid composition that may therefore be mentioned is one which comprises:

(i) DHA in an amount of from about 50% to about 85% by weight of the total fatty acid content of the composition;

(ii) ALA in an amount of from about 10% to about 90% by weight of the DHA; and (iii) a third polyunsaturated fatty acid in an amount of from about 10% to about 70% by weight of the ALA;

wherein the total amount of all other fatty acids in the composition is up to about 20% by weight of the total fatty acid content of the composition, wherein each of the DHA and the second and third polyunsaturated fatty acids is independently provided independently in the form of a fatty acid, a fatty acid salt, a fatty acid ester or a salt of a fatty acid ester; and wherein the amount of EPA in the composition is less than 10% by weight of the amount of DHA.

A further particular lipid composition that may be mentioned is one which comprises:

(i) DHA in an amount of from about 55% to about 80% by weight of the total fatty acid content of the composition;

(ii) ALA in an amount of from about 10% to about 60% by weight of the DHA; and (iii) a third polyunsaturated fatty acid selected from ETA and DPA in an amount of from about 10% to about 70% by weight of the ALA;

wherein the total amount of all other fatty acids in the composition is up to about 20% by weight of the total fatty acid content of the composition, wherein the DHA, the ALA, and the third polyunsaturated fatty acids are each independently provided in the form of a fatty acid, a fatty acid salt, a fatty acid ester or a salt of a fatty acid ester; and wherein the amount of EPA in the composition is less than 10% by weight of the amount of DHA.

In the compositions of the invention, the DHA and the second and third PUFAs may independently be present be in the form of a fatty acid, a fatty acid salt, a fatty acid ester or a salt of a fatty acid ester. In a particular embodiment, these components each take the same form, for example they may be all in the form of a fatty acid, all in the form of a fatty acid salt, all in the form of a fatty acid ester or all in the form of a salt of a fatty acid ester. Where the components are in the form of a fatty acid salt, ester or salt of an ester, then the components may be in the form of the same salt, ester or salt of the ester. For example, the DHA and the second and third PUFAs may be provided in the form of an ethyl ester of the fatty acid.

In a particular embodiment, the DHA and the second and third PUFAs are each independently provided in the form of a salt of a fatty acid ester or, most particularly, in the form of a fatty acid ester. Suitable fatty acid esters forms are known to the skilled person. For example, fatty acid ester forms that are nutritionally acceptable and/or pharmaceutically acceptable include ethyl esters, methyl esters, phospholipids, monoglycerides, diglycerides and triglycerides of fatty acids. Different ester forms may be required depending on the intended use of the lipid composition. For example, triglycerides are particularly suited for use in foods intended for human consumption, especially infant consumption, due in part to the taste and the stability of these ester forms to heat treatment (which may be necessary for such food products). Thus, in one embodiment, there is provided a food product for human or animal consumption comprising a lipid composition of the invention, wherein the DHA and the second and third polyunsaturated fatty acids are provided in the form of triglyceride esters. Ethyl esters are particularly suited for use in dietary supplements as these ester forms can be manufactured efficiently and easily, and conversion to a triglyceride form is not necessary. Thus, in a further embodiment, the DHA and the second and third PUFAs are each independently provided in the form of a fatty acid ethyl ester or as part of a triglyceride.

Triglycerides are esters derived from glycerol and three fatty acids. As the present invention concerns blends of fatty acids, the fatty acid components in such triglycerides may be mixed in the corresponding ratios. That is, while a mixture of different triglycerides molecules may be present in a composition, the overall fatty acid profile in the composition is as defined in the claims.

Fatty acid components may alternatively be present in the form of "free" fatty acids, i.e. the —COOH form of the fatty acid. However, in particular compositions of the invention, the compositions contain relatively low levels of fatty acids in this form because they are associated with an unpleasant (often "soapy") taste, and are less stable than fatty acids that are in an esterified form. Free fatty acids are typically removed from oils and lipid compositions by way of alkali or physical refining, e.g. according to processes discussed elsewhere herein. Thus, in one embodiment, the total free fatty acid content in the lipid compositions is less than 5% (such as less than 3%, particularly less than 2%) by weight of the total fatty acid content of the composition.

The fatty acids in the lipid compositions of the invention are typically linear (i.e. not branched) chain fatty acids. Compositions of the invention that may be mentioned include those which contain very low levels of branched chain fatty acids and their esters such that the composition is essentially free of branched chain fatty acids and branched chain fatty acid esters. By the terms "low levels", we mean that the composition contains branched chain fatty acids and fatty acid esters in an amount of at most about 0.1% by weight of the total fatty acids of the composition.

The lipid compositions of the invention may also contain other components (e.g. other than fatty acids) that originate from the source material and that are not fully removed during the extraction and enrichment process. The precise identities of those other components will vary greatly depending on the source material. Examples of such other components include phytosterols (i.e. plant sterols and plant stanols) present either as a free sterol or as a sterol ester (such as β-sitosterol, β-sitostanol, Δ5-avenasterol, campesterol, Δ5-stigmasterol, Δ7-stigmasterol and Δ7-avenasterol, cholesterol, brassicasterol, chalinasterol, campesterol, campestanol and eburicol). Other examples include antioxidants, such as tocopherols and tocotrienols. Thus, particular lipid compositions of the invention that may be mentioned include those which contain detectable quantities of one or more phytosterols (such as β-sitosterol). Such sterols may be present at at least about 0.01%, but typically not more than about 1%, by weight of the lipid composition.

The compositions of the present invention are advantageously obtainable from plant sources ("vegetable" sources). By the term "vegetable-based", we mean that at least 70% by weight of the lipids that are present in the compositions of the invention are obtained from vegetable sources. Vegetable sources include plant sources, particularly crops such as cereals. In at least one embodiment, lipids are obtained from a seed oil crop such as *Brassica*, for example *Brassica napus* or *Brassica juncea*. For the avoidance of doubt, however, it is not essential that the compositions be obtained solely from such sources, that is, a proportion (e.g. at most 30% by weight) of the lipids in the compositions of the invention may be obtained from other sources, including marine (e.g. fish or crustacea) oils, algal oils and mixtures thereof. In one example at least 80%, such as at least 90%, by weight of the lipids that are present are obtained from vegetable sources. In particular compositions of the invention, essentially all (i.e. at least 95%, at least 99%, or about 100%) of the lipids are obtained from vegetable sources.

In one embodiment, the compositions of the invention (and the feedstuffs and pharmaceutical compositions defined hereinafter) are not of animal (e.g. marine animal) origin. That is, in such embodiments the lipid compositions do not contain any components that are sourced from animals, such as fish and crustacea. Lipid compositions in which no components are obtained from an animal are believed to be advantageous in terms of lipid content, and a stability profile that can be achieved following standard refinement and/or enrichment procedures.

The use of plants as a lipid or fatty acid source offers a number of advantages. For example, marine sources of oils are known to contain relatively high levels of contaminants (such as mercury, PCBs and fish allergens (e.g. parvalbumins)) which are not found in plant materials. Historic overfishing has also depleted the stocks of fish and crustacea (e.g. krill) such that they are no longer sustainable. The present invention therefore offers a sustainably-sourced polyunsaturated fatty acid oil composition containing relatively low levels of unwanted contaminants.

In a particular embodiment, the composition of the invention is derived from a plant. Plants from which the oils are obtained are typically oilseed crops, such as copra, cottonseed, flax, palm kernel, peanut, rapeseed, soybean and sunflower seed. Compositions obtained exclusively from plants therefore may be referred to as "vegetable" oils or "vegetable lipid compositions". Suitable plants from which the lipid compositions of the invention may be obtained are known to the skilled person and include *Brassica* sp., *Gossypium hirsutum, Linum usitatissimum, Helianthus* sp., Carthamus tinctorius, *Glycine max, Zea mays, Arabidopsis thaliana, Sorghum bicolor, Sorghum vulgare, Avena sativa, Trifolium* sp., Elaesis guineenis, *Nicotiana benthamiana, Hordeum vulgare, Lupinus angustifolius, Oryza sativa, Oryza glaberrima, Camelina sativa*, or *Crambe abyssinica*. A particular plant source that may be mentioned in this respect is *Brassica* sp.

Suitable sources (including marine, algal and plant sources) may be naturally occurring, or may be genetically modified to enhance their ability to produce long chain polyunsaturated fatty acids. Examples of plant sources that have been genetically modified for this purpose, i.e. which originate from recombinant plant cells, are known to the skilled person and are disclosed in International patent application nos. PCT/AU2013/000639 (published as WO 2013/185184), PCT/AU2014/050433 (published as WO 2015/089587), and PCT/AU2015/050340 (published as WO 2015/196250). Genetically modified canola is described in WO 2017/218969 and WO 2017/219006. The disclosures in all of the publications mentioned herein are incorporated by reference in their entirety.

The lipid compositions of the invention may be obtained directly from a naturally occurring source (e.g. an animal, algae and/or a plant). However, it is typically necessary to processes the oils obtained from naturally occurring sources in order to enrich them. Suitable enrichment processes are exemplified in the Examples.

Suitable sources of lipid compositions of the invention, or "crude" oils which may be blended or enriched to produce those compositions, include marine species, algae and plants. Processes for obtaining oils from marine sources are well-known in the art.

Plant sources (such as oilseed sources) are particularly suited due to the low levels of certain contaminants and superior sustainability, as is discussed above. Plants such as *Brassica* sp. (e.g. canola) produce seeds which can be processed to obtain oil.

Extraction of Oils/Lipids

Techniques that are routinely practiced in the art can be used to extract, process, and analyse oils produced by plants and seeds. Typically, plant seeds are cooked, pressed, and oil extracted to produce crude oil. That oil may, in turn, be degummed, refined, bleached, and/or deodorised. A combination of degumming, refining, bleaching and deodorising has been found to be particularly effective for preparing LC-PUFA-enriched lipid mixtures. Thus, in one embodiment, the lipid composition is obtained from a seed oil that has been degummed, refined, bleached and/or deodorised. However, it is not necessary for the oils to be processed in this way and adequate purification and enrichment may be achieved without these methods.

Generally, techniques for crushing seed are known in the art. For example, oilseeds can be tempered by spraying them with water to raise the moisture content to, e.g., 8.5%, and flaked using a smooth roller with a gap setting of 0.23 mm to 0.27 mm. Depending on the type of seed, water may not be added prior to crushing. Extraction may also be achieved using an extrusion process. The extrusion process may or may not be used in place of flaking, and is sometimes used as an add-on process either before or after screw pressing.

In an embodiment, the majority of the seed oil is released by crushing using a screw press. Solid material expelled from the screw press is then extracted with a solvent, e.g. hexane, using a heat traced column, after which solvent is removed from the extracted oil. Alternatively, crude oil produced by the pressing operation can be passed through a settling tank with a slotted wire drainage top to remove the solids that are expressed with the oil during the pressing operation. The clarified oil can be passed through a plate and frame filter to remove any remaining fine solid particles. If desired, the oil recovered from the extraction process can be combined with the clarified oil to produce a blended crude oil. Once the solvent is stripped from the crude oil, the pressed and extracted portions are combined and subjected to normal oil processing procedures.

Refinement and Purification

As used herein, the term "purified" when used in connection with lipid or oil of the invention typically means that that the extracted lipid or oil has been subjected to one or more processing steps to increase the purity of the lipid/oil component. For example, purification steps may comprise one or more of: degumming, deodorising, decolourising, or drying the extracted oil. However, as used herein, the term "purified" does not include a transesterification process or another process that alters the fatty acid composition of the lipid or oil of the invention so as to increase the LC-PUFA content as a percentage of the total fatty acid content.

Expressed in other words, the fatty acid composition of the purified lipid or oil is essentially the same as that of the unpurified lipid or oil.

Plant oils may be refined (purified) once extracted from the plant source, using one or more of the following process, and particularly using a combination of degumming, alkali refining, bleaching and deodorisation. Suitable methods are known to those skilled in the art (e.g. those disclosed in WO 2013/185184).

Degumming is an early step in the refining of oils and its primary purpose is the removal of most of the phospholipids from the oil. Addition of ca. 2% of water, typically containing phosphoric acid, at 70 to 80° C. to the crude oil results in the separation of most of the phospholipids accompanied by trace metals and pigments. The insoluble material that is removed is mainly a mixture of phospholipids and triacylglycerols. Degumming can be performed by addition of concentrated phosphoric acid to the crude seedoil to convert non-hydratable phosphatides to a hydratable form, and to chelate minor metals that are present. Gum is separated from the seedoil by centrifugation.

Alkali refining is one of the refining processes for treating crude oil, sometimes also referred to as neutralisation. It usually follows degumming and precedes bleaching. Following degumming, the seedoil can be treated by the addition of a sufficient amount of an alkali solution to titrate all of the free fatty acids and phosphoric acid, and removing the soaps thus formed. Suitable alkaline materials include sodium hydroxide, potassium hydroxide, sodium carbonate, lithium hydroxide, calcium hydroxide, calcium carbonate and ammonium hydroxide. Alkali refining is typically carried out at room temperature and removes the free fatty acid fraction. Soap is removed by centrifugation or by extraction into a solvent for the soap, and the neutralised oil is washed with water. If required, any excess alkali in the oil may be neutralised with a suitable acid such as hydrochloric acid or sulphuric acid.

Bleaching is a refining process in which oils are heated at 90 to 120° C. for 10 to 30 minutes in the presence of a bleaching earth (0.2 to 2.0%) and in the absence of oxygen by operating with nitrogen or steam or in a vacuum. Bleaching is designed to remove unwanted pigments (carotenoids, chlorophyll, etc), and the process also removes oxidation products, trace metals, sulphur compounds and traces of soap.

Deodorisation is a treatment of oils and fats at a high temperature (e.g. ca. 180° C.) and low pressure (0.1 to 1 mm Hg). This is typically achieved by introducing steam into the seedoil at a rate of about 0.1 ml/minute/100 ml of seedoil. After about 30 minutes of sparging, the seedoil is allowed to cool under vacuum. This treatment improves the colour of the seedoil and removes a majority of the volatile substances or odorous compounds, including any remaining free fatty acids, monoacylglycerols and oxidation products.

Winterisation is a process sometimes used in commercial production of oils for the separation of oils and fats into solid (stearin) and liquid (olein) fractions by crystallization at sub-ambient temperatures. It was applied originally to cottonseed oil to produce a solid-free product. It is typically used to decrease the saturated fatty acid content of oils.

Transesterification

Crude oils usually contain the desired fatty acids in the form of triacylglycerols (TAGs). Transesterification is a process that can be used to exchange the fatty acids within and between TAGs or to transfer the fatty acids to another alcohol to form an ester (such as an ethyl ester or a methyl ester). In embodiments of the invention, transesterification is achieved using chemical means, typically involving a strong acid or base as a catalyst. Sodium ethoxide (in ethanol) is an example of a strong base that is used to form fatty acid ethyl esters through transesterification. The process may be performed at ambient temperature or at elevated temperature (e.g. up to about 80° C.).

In other embodiments of the invention, transesterification is achieved using one or more enzymes, particularly lipases that are known to be useful for hydrolysing ester bonds, e.g. in glycerides. The enzyme may be a lipase that is position-specific (sn-⅓ or sn-2 specific) for the fatty acid on the triacylglyceride, or that has a preference for some fatty acids over others. Particular enzymes that may be mentioned include Lipozyme 435 (available from Novozymes A/S). The process is typically performed at ambient temperature. The process is typically performed in the presence of an excess quantity of the alcohol corresponding to the desired ester form (e.g. by using ethanol in order to form ethyl esters of the fatty acids).

Distillation

Molecular distillation is an effective method for removing significant quantities of the more volatile components, such as the saturated fatty acids, from crude oils. Distillation is typically performed under reduced pressure, e.g. below about 1 mbar. The temperature and time may then be chosen to achieve an approximately 50:50 split between the distillate and residue after a distillation time of a few (e.g. 1 to 10) hours. Typical distillation temperatures used in the production of the lipid compositions of the present invention are in the region of 120° C. to 180° C., particularly between 145° C. and 160° C.

Multiple distillations may be performed, with each distillation being deemed complete when an approximately 50:50 split between the distillate and residue was achieved. The use of successive distillations reduces the overall yield, however two distillations may produce optimal results.

Chromatography

Chromatography is an effective method for separating the various components of LC-PUFA mixtures. It may be used to increase the concentration of one or more preferred LC-PUFAs within a mixture. Chromatographic separation can be achieved under a variety of conditions, but it typically involves using a stationary bed chromatographic system or a simulated moving bed system.

A stationary bed chromatographic system is based on the following concept: a mixture whose components are to be separated is (normally together with an eluent) caused to percolate through a column containing a packing of a porous material (the stationary phase) exhibiting a high permeability to fluids. The percolation velocity of each component of the mixture depends on the physical properties of that component so that the components exit from the column successively and selectively. Thus, some of the components tend to fix strongly to the stationary phase and thus will be more delayed, whereas others tend to fix weakly and exit from the column after a short while.

A simulated moving bed system consists of a number of individual columns containing adsorbent which are connected together in series and which are operated by periodically shifting the mixture and eluent injection points and also the separated component collection points in the system whereby the overall effect is to simulate the operation of a single column containing a moving bed of the solid adsorbent. Thus, a simulated moving bed system consists of columns which, as in a conventional stationary bed system, contain stationary beds of solid adsorbent through which eluent is passed, but in a simulated moving bed system the operation is such as to simulate a continuous countercurrent moving bed.

Columns used in these processes typically contain silica (or a modified silica) as the basis for the stationary phase. The mobile phase (eluent) is typically a highly polar solvent mixture, often containing one or more protic solvents, such as water, methanol, ethanol, and the like, as well as mixtures thereof. The eluent flow rate may be adjusted by the skilled person to optimise the efficiency of the separation process. For example, the products defined in the claims may be obtained using a relatively fast eluent flow rate. The use of slower flow rates may improve the degree of separation of the PUFAs contained in the initial mixture thus enabling higher concentrations of DHA to be obtained. Detection methods for LC-PUFAs are known to those skilled in the art, and include UV-vis absorption methods as well as refractive index detection methods.

According to a second aspect of the invention, there is therefore provided a process for producing a lipid composition of the invention, which process comprises providing a mixture of fatty acid ethyl esters; subjecting said mixture to a chromatographic separation process. The present invention also relates to lipid compositions that are obtainable by such processes. Suitable chromatographic separation conditions include those described herein.

For example, particular a particular mobile phase that may be used in the chromatographic separation is a mixture of methanol and water (e.g. 88% methanol/water), though this may be changed (e.g. to increase the methanol content) during the separation process to enhance the efficiency. A particular stationary phase that may be used is a silica-based stationary phase, such as a Deltaprep C18 column. Analytical HPLC, or any other suitable technique known to the person skilled in the art, may be performed on the fractions obtained to identify those that contain sufficiently high concentrations of the desired PUFAs, and thus contain the lipid compositions of the invention.

In an embodiment of the second aspect of the invention, the mixture of fatty acid ethyl esters is obtained by transesterification and distillation of a vegetable-based lipid oil, e.g. in accordance with any one of the processes hereinbefore described. The vegetable-based lipid oil may be obtained from any of the plants, particularly the oilseeds, disclosed herein or otherwise known in the art. Prior to transesterification and distillation, refinement of the vegetable-based lipid oil using degumming, alkali refinement, bleaching and/or deodorisation may optionally be performed.

Other Enrichment Methods

The lipid compositions of the present invention are useful as active pharmaceutical ingredients (APIs) or as precursors (or "intermediates") to APIs which may be obtained therefrom by way of further enrichment. Such compositions would be further enriched in the levels of beneficial PUFAs, such as DHA and/or ALA.

The concentration of polyunsaturated fatty acids in an oil can be increased by a variety of methods known in the art, such as, for example, freezing crystallization, complex formation using urea, supercritical fluid extraction and silver ion complexing. Complex formation with urea is a simple and efficient method for reducing the level of saturated and monounsaturated fatty acids in the oil. Initially, the TAGs of the oil are split into their constituent fatty acids, often in the form of fatty acid esters. These free fatty acids or fatty acid esters, which are usually unaltered in fatty acid composition by the treatment, may then be mixed with an ethanolic solution of urea for complex formation. The saturated and monounsaturated fatty acids easily complex with urea and crystallise out on cooling and may subsequently be removed by filtration. The non-urea complexed fraction is thereby enriched with long chain polyunsaturated fatty acids.

Products

The lipid compositions of the present invention are bulk oils. That is, the lipid composition has been separated from the source matter (e.g. plant seeds) from which some or all of the lipid was obtained).

The lipid compositions of the present invention can be used as feedstuffs. That is, the compositions of the invention may be provided in an orally available form. For purposes of the present invention, "feedstuffs" include any food or preparation for human consumption which when taken into the body serves to nourish or build up tissues or supply energy; and/or maintains, restores or supports adequate nutritional status or metabolic function. Feedstuffs include nutritional compositions for babies and/or young children such as, for example, infant formula. In the case of feedstuffs, the fatty acids may be provided in the form of triglycerides in order to further minimise any unpleasant tastes and maximise stability.

Feedstuffs comprise a lipid composition of the invention optionally together with a suitable carrier. The term "carrier" is used in its broadest sense to encompass any component which may or may not have nutritional value. As the skilled person will appreciate, the carrier must be suitable for use (or used in a sufficiently low concentration) in a feedstuff such that it does not have deleterious effect on an organism which consumes the feedstuff.

The feedstuff composition may be in a solid or liquid form. Additionally, the composition may include edible macronutrients, protein, carbohydrate, vitamins, and/or minerals in amounts desired for a particular use as are well-known in the art. The amounts of these ingredients will vary depending on whether the composition is intended for use with normal individuals or for use with individuals having specialised needs, such as individuals suffering from metabolic disorders and the like.

Examples of suitable carriers with nutritional value include macronutrients such as edible fats (e.g. coconut oil, borage oil, fungal oil, black current oil, soy oil, and mono- and diglycerides), carbohydrates (e.g. glucose, edible lactose, and hydrolysed starch) and proteins (e.g. soy proteins, electrodialysed whey, electrodialysed skim milk, milk whey, or the hydrolysates of these proteins).

Vitamins and minerals that may be added to the feedstuff disclosed herein include, for example, calcium, phosphorus, potassium, sodium, chloride, magnesium, manganese, iron, copper, zinc, selenium, iodine, and Vitamins A, E, D, C, and the B complex.

The lipid compositions of the present invention can be used in pharmaceutical compositions. Such pharmaceutical compositions comprise the lipid composition of the invention optionally together with one or more pharmaceutically-acceptable excipients, diluents or carriers, which are known to the skilled person. Suitable excipients, diluents or carriers include phosphate-buffered saline, water, ethanol, polyols, wetting agents or emulsions such as a water/oil emulsion. The composition may be in either a liquid or solid form, including as a solution, suspension, emulsion, oil or powder. For example, the composition may be in the form of a tablet, capsule, encapsulated gel, ingestible liquid (including an oil or solution) or powder, emulsion, or topical ointment or cream. The pharmaceutical composition may also be provided as an intravenous preparation.

Particular forms suitable for feedstuffs and for pharmaceutical compositions include liquid-containing capsules and encapsulated gels.

The lipid compositions of the invention may be mixed with other lipids or lipid mixtures (particularly vegetable-based fatty acid esters and fatty acid ester mixtures) prior to use. The lipid compositions of the invention may be provided together with one or more additional components selected from the group consisting of an antioxidant (e.g. a tocopherol (such as alpha-tocopherol or gamma-tocopherol) or a tocotrienol), a stabiliser, and a surfactant. Alpha-tocopherol and gamma-tocopherol are both naturally occurring components in various plant seed oils, including canola oils.

It may also be desirable to include isotonic agents, for example, sugars, sodium chloride, and the like. Besides such inert diluents, the composition can also include adjuvants, such as wetting agents, emulsifying and suspending agents, sweetening agents, flavouring agents and perfuming agents. Suspensions, in addition to the lipid compositions of the invention, may comprise suspending agents such as ethoxylated isostearyl alcohols, polyoxyethylene sorbitol and sorbitan esters, microcrystalline cellulose, aluminium metahydroxide, bentonite, agar-agar, and tragacanth or mixtures of these substances.

Solid dosage forms such as tablets and capsules can be prepared using techniques well known in the art. For example, fatty acids produced in accordance with the methods disclosed herein can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with the relevant lipid composition and optionally one or more antioxidants.

Possible routes of administration of the pharmaceutical compositions of the present invention include, for example, enteral (e.g., oral and rectal) and parenteral. For example, a liquid preparation may be administered orally or rectally. Additionally, a homogenous mixture can be completely dispersed in water, admixed under sterile conditions with physiologically acceptable diluents, preservatives, buffers or propellants to form a spray or inhalant.

The lipid compositions of the invention are indicated as pharmaceuticals. According to a further aspect of the invention there is provided a composition of the invention, including any of the pharmaceutical compositions described hereinabove, for use as a pharmaceutical.

Lipid compositions of the invention may provide a number of benefits that are typically associated with long-chain polyunsaturated fatty acids. For example, the lipid compositions of the invention, and the pharmaceutical compositions described hereinabove, may be used in the treatment or prevention of cardiovascular disease, protection against death in patients with cardiovascular disease, reduction of overall serum cholesterol levels, reduction in high BP, increase in HDL:LDL ratio, reduction of triglycerides, or reduction of apolipoprotein-B levels, as may be determined using tests that are well-known to the skilled person. Accordingly, methods of treating (or preventing) the diseases and conditions listed above using the lipid compositions of the invention are also disclosed.

As used herein, the terms "treatment," "treat," and "treating" refer to reversing, alleviating, inhibiting the progress of a disease or disorder as described herein, or delaying, eliminating or reducing the incidence or onset of a disorder or disease as described herein, as compared to that which would occur in the absence of the measure taken. As used herein, the terms "prevent", "prevention" and "preventing" refer to the reduction in the risk of acquiring or developing a given condition, or the reduction or inhibition of the recurrence or said condition in a subject who is not ill.

A typical dosage of a particular fatty acid is from 0.1 mg to 20 g, taken from one to five times per day (up to 100 g daily) and is particularly in the range of from about 10 mg to about 1, 2, 5, or 10 g daily (taken in one or multiple doses). As known in the art, a minimum of about 300 mg/day of fatty acid, especially LC-PUFA, is desirable. However, it will be appreciated that any amount of fatty acid will be beneficial to the subject.

When used as a pharmaceutical composition, the dosage of the lipid composition to be administered to the patient may be determined by one of ordinary skill in the art and depends upon various factors such as weight of the patient, age of the patient, overall health of the patient, past history of the patient, immune status of the patient, etc.

The compositions of the invention are readily obtainable compositions which may have an improved stability profile and which may contain a mixture of fatty acids in which the relative proportions of omega-3 and omega-6 fatty acids are particularly beneficial for human health. Stability may be assessed using a variety of methods known to those skilled in the art. Such methods include the Rancimat method, the assessment of propanal formation (particularly appropriate for omega-3 fatty acids), the assessment of hexanal formation (particularly appropriate for omega-6 fatty acids), the "peroxide value" method (e.g. using AOCS official method Cd 8-53) and the "p-anisidine value" method (e.g. using AOCS official method Cd 18-90). It is shown in the Examples that the compositions of the invention are obtainable from starting mixtures which do not show an enhanced stability profile in comparison to reference blends (the reference blends having a similar composition in terms of the key LC-PUFAs but containing a significant quantity of lipid of animal (fish) origin).

The compositions of the invention may also have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, lipid compositions known in the prior art.

Figure 2:
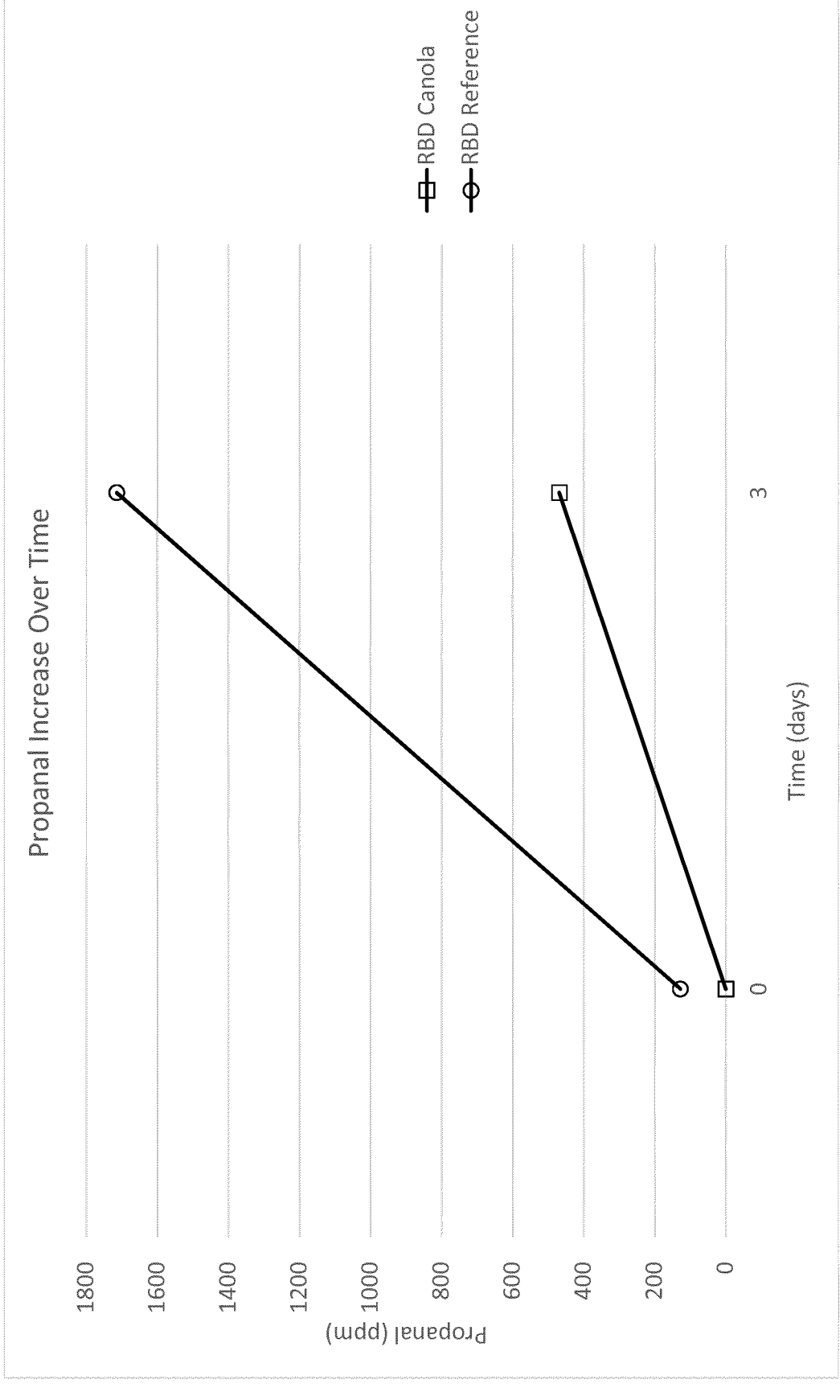

The invention is illustrated by the following examples in which:

FIG. 1 shows propanal release data for the canola oil and reference oil (following transesterification, distillation and chromatography), demonstrating the improved stability of the canola oil described herein; and FIG. 2 shows propanal release data for the canola oil and reference oil (following RBD refinement, transesterification, distillation and chromatography), demonstrating the improved stability of the canola oil described herein.

EXAMPLES

Example 1—DHA Canola Oil Extraction from Seeds

Canola of a variety disclosed in US patent publication no. US 2018/0016590 A1 was grown as a summer crop. The seed was harvested and then stored at room temperature prior to crushing.

272 kg of the seed was crushed to produce DHA oil using a Kern Kraft KK80 screw press. The expeller collar heater temperature was set to the maximum set temperature on the thermostat. Initial ambient and choke temperature was 20° C. and the choke distance was set at 73.92 mm. The seed was fed with continual oil and meal collection without stopping the expeller till all the seed was crushed.

The speed of rotation of the auger, the temperature of the meal and expelled oil were monitored throughout the pressing. The crush time was 4 hours for 270 kg which is a throughput rate of 67.5 kg/hr. A yield of 87.2 kg (32%) crude oil was obtained. After filtering to remove fines, the yield was 77.2 kg (28%).

Example 2—Reference Blend Oil

Pure fish oil contains low levels of ALA fatty acids and significantly higher levels of EPA and DHA. A reference oil blend (referred to herein as the "crude triglyceride reference blend oil" or similar) was designed to be as similar as possible in composition to the filtered DHA Canola oil obtained in Example 1. This was done by (a) matching the total level of DHA to that in the DHA Canola oil and (b) matching the ratio of DHA/(ALA+EPA). This was achieved by blending a fish oil rich in DHA (tuna), an oil rich in ALA (flaxseed oil) and standard Canola oil. The resulting reference blend oil also has a similar total omega-3 content to the DHA Canola oil.

Example 3—Fatty Acid Compositions of the Crude DHA Canola Oil and Reference Blend The fatty acid compositions of the filtered crude oil and the reference blend oil were analysed. The results are shown below.

| Fatty Acid | | Crude DHA Canola oil (wt %) | Crude Reference oil (wt %) |
|---|---|---|---|
| Palmitic | C16:0 | 4.3 | 9.6 |
| Stearic | C18:0 | 1.9 | 3.8 |
| Oleic | C18:1n9c | 39.4 | 30.6 |
| Cis-vaccenic | C18:1n7c | 3.6 | 2.0 |
| Linoleic | C18:2n6c | 7.8 | 11.5 |
| GLA | C18:3n6 | 0.1 | 0.1 |
| ALA | C18:3n3 | 21.9 | 21.2 |
| Arachidic | C20:0 | 0.7 | 0.4 |
| SDA | C18:4n3 | 2.2 | 0.2 |
| Gondoic | C20:1n9c | 1.4 | 0.8 |
| Behenic | C22:0 | 0.3 | 0.2 |
| ETA | C20:4n3 | 1.0 | 0.1 |
| Erucic | C22:1n9c | 0.0 | 0.1 |
| EPA | C20:5n3 | 0.4 | 1.7 |
| DPA3 | C22:5n3 | 0.9 | 0.4 |
| DHA | C22:6n3 | 10.2 | 9.8 |
| | Other | 4.0 | 7.6 |

Example 4—Oil Stability Assessment

A Rancimat stability study was performed using the crude DHA canola oil and reference blend described in Examples 1 and 2, respectively. The method involved testing about 2.5 g of test material using the standard procedures for a Metrohm 743 Rancimat at 90° C.

The table below summarises the results obtained from these oils at 90° C. The experiments were performed in duplicate.

| Oil | Time | |
|---|---|---|
| DHA Canola oil | 7 hrs 29 min | 7 hrs 17 min |
| Reference oil | 10 hrs 26 min | 10 hrs 11 min |

The DHA canola oil showed consistently poorer stability than the reference oil.

Example 5—Enzymatic Trans-Esterification of Crude Canola-DHA Oil

The following enzymatic trans-esterification procedure was performed on approx. 5 kg of the crude triglyceride oil obtained in Example 1. Lipozyme 435 was obtained from Novozymes A/S.

To a dry, nitrogen flushed reactor fitted with a mechanical stirrer was added 100% undenatured ethanol (5.00 kg) and the crude triglyceride oil obtained in Example 1 (5.00 kg) and the mixture stirred. To this mixture was added Lipozyme 435 (420 g) and the mixture heated at 40° C. for 21 hr. A $^1$H NMR spectrum recorded of a sample taken from the mixture indicated the reaction was complete.

The mixture was cooled to 20° C. The mixture was drained from the reactor and filtered through a 4 μm polypropylene filter cloth on a 20 L Neutsche filter. The reactor was rinsed with ethanol (2×1.6 L) and pet. spirit (2.51) and these used to sequentially wash the filter cake. To the resulting crude reaction mixture was added pet. spirit (10 L) and water (4 L) and the mixture thoroughly mixed in the reactor and then allowed to stand, after which 2 phases formed.

The pet. spirit layer was removed and the aqueous layer further extracted with pet. spirit (2×10 L). The combined pet. spirit layers were returned to the reactor and evaporated in vacuo to low volume (approx. 10 L). The resulting concentrated solution was drained from the reactor, dried over anhydrous magnesium sulphate (approx. 1 kg), filtered and concentrated in vacuo to give a yellow oil (yield: 99%).

Example 6—Enzymatic Trans-Esterification of Crude Reference Blend Oil

Enzymatic transesterification of the crude triglyceride reference blend oil obtained according to Example 2 (5.00 kg) was completed using the process described in the preceding Example. The product was obtained as a yellow oil.

Example 7—Distillation of Transesterified Canola Oils

Standard Procedure for the Removal of More Volatile Components of Fatty Acid Ethyl Esters (FAEE) Mixtures by Vacuum Distillation The crude fatty acid ethyl esters (FAEE) from the crude canola-DHA (obtained in Example 5) were subjected to distillation under the following conditions. Separation by distillation was achieved by passing the trans-esterified crude oil through a Pope 2 inch (50 mm) wiped film still under vacuum equipped with 2×1000 ml collection flasks collecting the distillate and residue. Each was analysed for fatty acid composition.

Vacuum was supplied by an Edwards 3 rotary pump and the vacuum measured by an ebro vacumeter VM2000.

The oil was fed into the still by a Cole-Palmer Instrument Company easy-load II peristaltic pump at 4 mL/min with the still motor set to 325 rpm with water condenser used to condense the distillate. The feed was continued until such time as one or other of the receiver flasks was full.

Crude canola-DHA FAEE was distilled under these conditions with the heater bands initially set to 147° C. The objective was to obtain a 50:50 split of distillate:residue. During the first 30-45 minutes of the experiment, the temperature of the heater bands was increased to 154° C. to increase the proportion of the oil that distilled and the still then allowed to equilibrate. After half an hour, the temperature of the heater bands was adjusted over half an hour down to 149° C. The remainder of the distillation took place at 149° C. The total time of distillation was 350 minutes. A portion of the residue from the above distillation was again subjected to the removal of more volatile components by distillation under the standard conditions with the temperature of the heater bands set to 149° C. The total time of distillation was 95 minutes.

| Distillation | Feed | Distillate | Residue |
|---|---|---|---|
| First | 1395.4 g | 699.5 g | 690.5 g |
| Second | 376.3 g | 211.7 g | 160.3 g |

Example 8—Distillation of Transesterified Crude Reference Blend-Derived FAEE

The crude fatty acid ethyl esters (FAEE) from the crude reference blend (obtained in Example 6) were subjected to distillation under the same conditions as shown in the preceding Example.

Crude reference blend FAEE was distilled under these standard conditions with the heater bands initially set to 152° C. The objective was to obtain a 50:50 split of distillate:residue. After 20 minutes the temperature of the heater bands was set to 154° C. to increase the flow of distillate. After a further hour the heater bands temperature was adjusted to 153° C. and then 152° C. over the next hour. For the last hour of the distillation the heater bands temperature was set to 153° C. The total time of distillation was 380 minutes. The residue from the above distillation was again subjected to the removal of more volatile components by distillation under the standard conditions. The objective was to obtain a 50:50 split of distillate:residue. The distillation was mostly performed with the heater bands set to 150-151° C. The total time of distillation was 195 minutes.

| Distillation | Feed | Distillate | Residue |
|---|---|---|---|
| First | 1515.7 g | 729.6 g | 775.1 g |
| Second | 768.5 g | 399.7 g | 363.3 g |

Example 9—Chromatographic Separation of Canola-Derived FAEE

Preparative HPLC

The fatty acid ethyl esters (FAEE) obtained in Example 7 (i.e. that had been obtained from the crude canola-DHA and processed using transesterification and distillation) were subjected to chromatographic separation under the following conditions. A preparative HPLC system comprising a Waters Prep 4000 system, Rheodyne injector with 10 ml loop, 300×40 mm Deltaprep C18 column, Waters 2487 dual wavelength detector and chart recorder was equilibrated with 88% methanol/water mobile phase at 70 mL/min. The detector was set to 215 nm and 2.0 absorbance units full scale and the chart run at 6 cm/hr.

1.0 g of FAEE oil was dissolved in a minimum amount of 88% methanol/water and injected onto the column via the Rheodyne injector. Approximately 250 mL fractions were collected once the solvent front appeared after around 7 minutes.

Analytical HPLC was performed on all the fractions, and the "symmetrical" fractions containing predominantly DHA were combined (yield: 28%).

Analytical HPLC

An HPLC system comprising a Waters 600E pump controller, 717 autosampler, 2996 photodiode array detector and 2414 refractive index detector was used for sample analysis. The analysis was performed on a 150×4.6 mm Alltima C18 column using either isocratic 90% methanol/water or 95% methanol/water at 1.0 mL/min as mobile phase. Data collection and processing was performed in Waters Empower 3 software.

Example 10—Chromatographic Separation of Reference Blend-Derived FAEE

The distilled fatty acid ethyl esters (FAEE) of the reference blend (obtained in Example 8) were subjected to chromatographic separation under the same conditions as shown in the preceding Example.

Analytical HPLC was performed on all the fractions, and the "symmetrical" fractions containing predominantly DHA were combined.

Example 11—Fatty Acid Composition Analysis for the Enriched Oils

The fatty acid compositions of the products obtained in Examples 9 and 10 were analysed. The results are shown below.

| Fatty Acid | | DHA Canola oil (wt %) (Example 9) | Reference oil (wt %) (Example 10) |
|---|---|---|---|
| Palmitic | C16:0 | 0.00 | 0.00 |
| Stearic | C18:0 | 0.00 | 0.00 |
| Oleic | C18:1n9c | 0.00 | 0.00 |
| Cis-vaccenic | C18:1n7c | 0.00 | 0.00 |
| Linoleic | C18:2n6c | 1.65 | 1.80 |
| GLA | C18:3n6 | 0.63 | 0.00 |
| ALA | C18:3n3 | 29.35 | 31.42 |
| Arachidic | C20:0 | 0.00 | 0.00 |
| SDA | C18:4n3 | 0.00 | 0.00 |
| Gondoic | C20:1n9c | 0.00 | 0.00 |
| | C20:3n3 | 0.00 | 0.00 |
| Behenic | C22:0 | 0.00 | 0.00 |
| ETA | C20:4n3 | 3.77 | 2.43 |
| Erucic | C22:1n9c | 0.00 | 0.00 |

| Fatty Acid | | DHA Canola oil (wt %) (Example 9) | Reference oil (wt %) (Example 10) |
|---|---|---|---|
| EPA | C20:5n3 | 1.42 | 6.49 |
| DPA6 | C22:5n6 | 0.14 | 1.03 |
| DPA3 | C22:5n3 | 0.47 | 0.37 |
| DHA | C22:6n3 | 60.94 | 54.03 |
| Other | | 1.63 | 2.43 |

Example 12—Oil Stability Assessment

Headspace GC-MS Stability Trial

Headspace analysis was conducted on the enriched products described above to assess the quantities of propanal that are released under specific conditional. Increased levels of propanal release demonstrate reduced stability for the test material.

SPME (Solid-Phase Microextraction) Method:

Selected 65 μm PDMS/DVB StableFlex fiber (Supelco fiber kit 57284-u)

Fibers were conditioned for 10 mins prior to use at 250° C. in a Triplus RSH conditioning station Samples were incubated at 40° C. for 1 min prior to extraction.

Extracted for 1 min from Headspace vial

Expected to be a good general method capable of capturing a wide range of volatile components.

Gc Method:

Thermo Scientific TRACE 1310 GC

Thermo Scientific TR-DIOXIN 5 MS column, 0.25 mm internal diameter, 30 m film 0.1 μm Split injection 250° C. Split 83, 1.2 ml He/min GC Ramp: 40° C. 1 min to 100 at 5° C./min, then to 300° C. at 50° C./min A generic MS specific column with good synergy for headspace analysis was used. A slow initial temperature ramp was employed to maximise separation of volatiles before ramping up to maximum to maintain column performance. Split injections were employed to avoid the requirement for cryogenic cooling of the inlet and enhance column resolution.

Separation of the standards was hampered by some peak overlap but could still be accommodated in the quantitation. 3 standard calibration results (0.1, 0.01 and 0.01%), the molecular ion m/z 56 was employed for detection of propanal. The base peak at m/z 58 is used to detect hexanal.

Ms Method:

Thermo Scientific DFS high resolution GC-MS

Low resolution (1000), full scan 35-350 Da at 0.5 s/scan

Standards:—Propanal and Hexanal standard dilutions were made into DHA Canola Ethyl esters supplied. These Standard mixtures were then added at a volume of 540 μl to 20 ml headspace vials.

Full scan was employed, allowing the monitoring of all evolved products rather than specific molecules.

Headspace Stability Results:

The table below summarises the results obtained from the canola oil obtained in Example 9 and the reference oil obtained in Example 10 from T=0 to 5 days. Test samples were held during this period at ambient temperature on a light box and under fluorescent tube lighting. The m/z 58 molecular ion was analysed, and the mass chromatogram clearly shows emergence of propanal at RT 1.37 mins. Propanal development is quantified in the table below, and the data are shown in FIG. 1. The DHA canola oil released substantially lower amounts of propanal demonstrating the improved stability of the canola oil as compared to the reference.

| Time point (days) | 0 | 5 |
|---|---|---|
| DHA Canola oil (ppm propanal) | 327.613 | 2371.063 |
| Reference oil (ppm propanal) | 1678.681 | 3729.451 |

The DHA Canola oil showed superior stability to oxidation compared with the reference oil.

Example 13—Refinement of DHA Canola Oil

A portion of the canola oil obtained in Example 1 was refined prior to undergoing further enrichment. The refinement process involved degumming, alkali refinement, bleaching and deodorisation.

Acid Degumming

Degumming is the removal of non-hydratable and hydratable phosphatides from the oil. The dried crude oil obtained in Example 1 was heated to 53±2° C. and 0.2% of a 50% citric acid solution was added. After approximately 30 minutes of mixing, 2.0% of heated (53±2° C.) softened water was added and mixed for approximately 30 minutes. The oil was heated to 67±3° C. during the hold and then centrifuged.

Acid Pretreat/Refining

Refining is the removal of free fatty acids following their saponification with caustic to make them water-soluble and their subsequent removal by centrifugation. An acid pretreatment step was used to continue the hydration of the phosphatides. The degummed oil was heated to 65±5° C. and 0.1% of 85% phosphoric acid added, and mixed for a total of 30 minutes. After the acid addition and hold time, 20 Be' (Baume; 14.4%, w/w) sodium hydroxide was added to neutralise the free fatty acids plus a 0.05% (w/w) excess. The caustic and oil were then mixed for an additional 15 minutes. The oil was heated to 62±2° C. during the 15-minute hold, and then the oil was centrifuged.

Trisyl Silica Treatment

Trisyl silica treatment was performed for the further removal of soaps, to levels compatible with bleaching. Trisyl pretreatment was combined with the bleaching step. The refined oil was heated to 68±5° C. and treated with 0.3% of Trisyl 300. The oil/Trisyl was mixed for approximately 15 minutes, and then bleaching was continued.

Bleaching

Refined oil was treated with adsorptive clay for the removal of peroxides, phosphatides, colour bodies and traces of soap. An acid pretreatment step was used to continue the hydration of the phosphatides. The Trisyl pretreated oil was mixed with 0.2% (w/w) of a 50% acid solution. After 15 minutes of mixing, 2% (w/w) of Tonsil Supreme 126 FF bleaching clay was added. The mixture was then heated to 90±2° C. under vacuum and held for approximately 30 minutes. The oil was cooled to 60±2° C., vacuum broken with nitrogen, 1.0 kg of filter aid added and filtered. Pressure Vessel: 500 L Cherry-Burrell pressure vessel, steam or cooling water jacket, all 316 stainless construction with impeller and baffles for mixing, mfg's serial #E-227-94. Filter Press: 24" Polypropylene Sperry Filter Press, capacity 4.8 cu ft filter, paper and cloth supports were used.

Deodorizing

The bleached oil was subjected to sparging with steam at high temperature and low pressure to remove odoriferous components, flavour components, and additional free fatty acids. Colour is also reduced by heat bleaching at elevated temperatures. The half of the bleached oil was deodorised at 180±2° C. for 60 min with 1% sparge steam and Fatty Acid Composition (FAC) was monitored. Deodoriser Vessel (OD4): 400 L Coppersmithing vacuum rated vessel, steam or cooling water jacket, all 316 stainless construction. A slight decrease of DHA level was observed at 180° C. for 60 min hold. Then another trial was conducted at 180° C. for 30 min hold. The product was packaged under nitrogen in 20-L plastic HDPE pails and stored in a cooler at 4° C.

Example 14—Refinement of Original Reference Blend Oil

A portion of the reference blend described in Example 2 was refined prior to undergoing further enrichment. In the refinement process the reference blend was subjected to refinement under the same conditions as shown in the preceding Example.

Example 15—Fatty Acid Compositions of the RBD Crude DHA Canola Oil and Reference Blend The fatty acid compositions of the RBD filtered crude oil (of Example 13) and the RBD reference blend oil (of Example 14) were analysed. The results are shown below.

| Fatty Acid | | Crude DHA Canola oil (wt %) | Crude Reference oil (wt %) |
|---|---|---|---|
| Palmitic | C16:0 | 4.23 | 9.22 |
| Stearic | C18:0 | 2.52 | 3.89 |
| Oleic | C18:1n9c | 42.90 | 31.62 |
| Cis-vaccenic | C18:1n7c | 3.01 | 1.96 |
| Linoleic | C18:2n6c | 7.15 | 12.18 |
| GLA | C18:3n6 | 0.54 | 0.00 |
| ALA | C18:3n3 | 19.95 | 22.51 |
| Arachidic | C20:0 | 0.72 | 0.38 |
| SDA | C18:4n3 | 2.25 | 0.17 |
| Gondoic | C20:1n9c | 1.28 | 0.71 |
| Behenic | C22:0 | 0.31 | 0.22 |
| ETA | C20:4n3 | 1.08 | 0.00 |
| Erucic | C22:1n9c | 0.00 | 0.00 |
| EPA | C20:5n3 | 0.47 | 1.67 |
| DPA3 | C22:5n3 | 0.96 | 0.41 |
| DHA | C22:6n3 | 9.33 | 9.20 |
| | Other | 3.32 | 5.86 |

References to "RBD" in connection with the Examples (and the accompanying figures) mean that the product in question was obtained directly or indirectly from the "refined" products of either Example 13 (for Canola oils) and Example 14 (for reference blends).

Example 16—Enzymatic Trans-Esterification of RBD Canola-DHA Oil

Enzymatic transesterification of the crude triglyceride reference blend oil obtained according to Example 13 (5 kg) was completed using the process described in Example 5. The product was obtained as a yellow oil.

Example 17—Enzymatic Trans-Esterification of RBD Reference Blend Oil

Enzymatic transesterification of the crude triglyceride reference blend oil obtained according to Example 14 (5 kg) was completed using the process described in Example 5. The product was obtained as a yellow oil.

Example 18—Distillation of Transesterified RBD Canola Oils

Standard Procedure for the Removal of More Volatile Components of Fatty Acid Ethyl Esters (FAEE) Mixtures by Vacuum Distillation The fatty acid ethyl esters (FAEE) from the RBD canola-DHA (obtained in Example 16) were subjected to distillation under the following conditions. Separation by distillation was achieved by passing the trans-esterified crude oil through a Pope 2 inch (50 mm) wiped film still under vacuum equipped with 2×1000 ml collection flasks collecting the distillate and residue. Each was analysed for fatty acid composition.

Vacuum was supplied by an Edwards 3 rotary pump and the vacuum measured by an ebro vacumeter VM2000.

The oil was fed into the still by a Cole-Palmer Instrument Company easy-load II peristaltic pump at 4 mL/min with the still motor set to 325 rpm with water condenser used to condense the distillate. The feed was continued until such time as one or other of the receiver flasks was full.

RBD canola-DHA FAEE was distilled under these conditions with the heater bands initially set to 152° C. to obtain a 50:50 split of distillate:residue. A portion of the residue from this distillation was again subjected to the removal of more volatile components by distillation under the standard conditions with the temperature of the heater bands set to 152° C. The total time of distillation was approx. 90 minutes.

| Distillation | Feed | Distillate | Residue |
|---|---|---|---|
| First | 1596.6 | 729.9 | 855.9 |
| Second | 851.3 | 503.5 | 343.1 |

Example 19—Distillation of Transesterified RBD Reference Blend-Derived FAEE

The fatty acid ethyl esters (FAEE) from the RBD reference blend (obtained in Example 17) were subjected to distillation under the same conditions as shown in the preceding Example.

RBD reference blend FAEE was distilled under these standard conditions with the heater bands initially set to 152° C. to obtain a 50:50 split of distillate:residue. The residue from this distillation was again subjected to the removal of more volatile components by distillation under the standard conditions. The objective was to obtain a 50:50 split of distillate:residue. The distillation was mostly performed with the heater bands set to 152° C. The total time of distillation was approx. 200 minutes.

| Distillation | Feed | Distillate | Residue |
|---|---|---|---|
| First | 1195.1 | 674.7 | 504.6 |
| Second | 496.4 | 297.2 | 197.4 |

Example 20—Chromatographic Separation of RBD Canola-Derived FAEE

The fatty acid ethyl esters (FAEE) obtained in Example 18 (i.e. that had been obtained from the RBD canola-DHA and processed using transesterification and distillation) were subjected to chromatographic separation under the following conditions. A preparative HPLC system comprising a Waters Prep 4000 system, Rheodyne injector with 10 ml loop, 300×40 mm Deltaprep C18 column, Waters 2487 dual wavelength detector and chart recorder was equilibrated with 88% methanol/water mobile phase at 70 mL/min. The detector was set to 215 nm and 2.0 absorbance units full scale and the chart run at 6 cm/hr.

1.0 g of FAEE oil was dissolved in a minimum amount of 88% methanol/water and injected onto the column via the Rheodyne injector. Approximately 250 mL fractions were collected once the solvent front appeared after around 7 minutes.

Analytical HPLC was performed on all the fractions, and the "symmetrical" fractions containing predominantly DHA were combined.

Example 21—Chromatographic Separation of RBD Reference Blend-Derived FAEE

The distilled fatty acid ethyl esters (FAEE) of the RBD reference blend (obtained in Example 19) were subjected to chromatographic separation under the same conditions as shown in the preceding Example.

Analytical HPLC was performed on all the fractions, and the "symmetrical" fractions containing predominantly DHA were combined.

Example 22—Fatty Acid Composition Analysis for the Enriched RBD Oils

The fatty acid compositions of the products obtained in Examples 20 and 21 were analysed. The results are shown below.

| | Fatty Acid | DHA Canola oil (wt %) (Example 20) | Reference oil (wt %) (Example 21) |
|---|---|---|---|
| Palmitic | C16:0 | 0.00 | 0.00 |
| Stearic | C18:0 | 0.00 | 0.00 |
| Oleic | C18:1n9c | 0.00 | 0.00 |
| Cis-vaccenic | C18:1n7c | 0.00 | 0.00 |
| Linoleic | C18:2n6c | 7.12 | 9.58 |
| GLA | C18:3n6 | 0.15 | 0.00 |
| ALA | C18:3n3 | 11.83 | 10.72 |
| Arachidic | C20:0 | 0.00 | 0.00 |
| SDA | C18:4n3 | 0.00 | 0.00 |
| Gondoic | C20:1n9c | 0.00 | 0.00 |
| Behenic | C22:0 | 0.00 | 0.00 |
| ETA | C20:4n3 | 4.15 | 0.43 |
| Erucic | C22:1n9c | 0.00 | 0.00 |
| EPA | C20:5n3 | 0.00 | 0.18 |
| DPA3 | C22:5n3 | 7.34 | 3.40 |
| DHA | C22:6n3 | 65.55 | 70.63 |
| | Other | 3.86 | 5.06 |

Example 24—Oil Stability Assessment

Headspace analysis was conducted on the enriched products described in Examples 20 and 21 accordance with the method described in Example 12.

The table below summarises the results obtained from the RBD canola oil obtained in Example 20 and the RBD reference oil obtained in Example 21 from T=0 to 3 days. Test samples were held during this period at ambient temperature on a light box and under fluorescent tube lighting. The m/z 58 molecular ion was analysed, and the mass chromatogram clearly shows emergence of propanal at RT 1.37 mins. Propanal development is quantified in the table below, and the data are shown in FIG. 2. The DHA canola oil released substantially lower amounts of propanal demonstrating the improved stability of the canola oil as compared to the reference.

| Time point (days) | 0 | 3 |
|---|---|---|
| DHA Canola oil (ppm propanal) | 0.000 | 469.000 |
| Reference oil (ppm propanal) | 128.000 | 1714.000 |

The DHA Canola oil showed superior stability to oxidation compared with the reference oil.

The invention claimed is:

1. A vegetable-based lipid composition comprising:
(i) docosahexaenoic acid (22:6n-3) (DHA) in an amount of from 50% to 85% by weight of the total fatty acid content of the composition;
(ii) a second polyunsaturated fatty acid in an amount of from 10% to 90% by weight of the DHA; and
(iii) a third polyunsaturated fatty acid in an amount of from 10% to 70% by weight of the second polyunsaturated fatty acid;
wherein the total amount of all other fatty acids in the composition is up to 20% by weight of the total fatty acid content of the composition, wherein the second or third polyunsaturated fatty acid is eicosatetraenoic acid (20:4n-3) (ETA), wherein each of the docosahexaenoic acid, and the second and third polyunsaturated fatty acids is independently provided in the form of a fatty acid, a fatty acid salt, a fatty acid ester or a salt of a fatty acid ester; wherein the amount of eicosapentaenoic acid (EPA) in the composition is less than 10% by weight of the amount of DHA, wherein the ratio of omega-3 fatty acids to omega-6 fatty acids in the composition is at least 10:1, wherein the composition contains less than 0.5% palmitic acid (C16:0) by weight of the total fatty acid in the composition; and wherein the lipids present in the composition are obtained from plant sources.

2. The lipid composition of claim 1, wherein the docosahexaenoic acid is present in an amount that is at least 55% by weight of the total fatty acid content of the composition.

3. The lipid composition of claim 1, wherein the second polyunsaturated fatty acid is present in an amount of from 10% to 60% by weight of the docosahexaenoic acid.

4. The lipid composition of claim 1, wherein the second polyunsaturated fatty acid is a C18-24 omega-3 polyunsaturated fatty acid containing at least three unsaturations.

5. The lipid composition of claim 1, wherein the third polyunsaturated fatty acid is present in an amount of from 10% to 65% by weight of the second polyunsaturated fatty acid.

6. The lipid composition of claim 1, wherein the third polyunsaturated fatty acid is a C18-24 omega-3 polyunsaturated fatty acid containing at least three unsaturations.

7. The lipid composition of claim 1, wherein the DHA and the second and third polyunsaturated fatty acids are each independently provided in the form of a fatty acid ester or a salt of a fatty acid ester, wherein the fatty acid ester or salt of the fatty acid ester is a fatty acid ethyl ester or part of a triglyceride.

8. The lipid composition of claim 1, wherein the lipid composition is derived from a single source.

9. The lipid composition of claim 1, wherein the plant-based oil is from an oilseed selected from *Brassica* sp., *Gossypium hirsutum, Limum usitatissimum, Helianthus* sp., Carthamus tinctorius, *Glycine max, Zea mays, Arabidopsis thaliana, Sorghum bicolor, Sorghum vulgare, Avena sativa, Trifolium* sp., *Elaeis guineensis, Nicotiana benthamiana, Hordeum vulgare, Lupimis angustifolius, Oryza sativa, Oryza glaberrima, Camelina sativa*, or *Crambe abyssinica*.

10. The lipid composition of claim 1, wherein the composition is provided in the form of a tablet, capsule, encapsulated gel, ingestible liquid or powder, emulsion, or a topical ointment or cream.

11. The lipid composition of claim 1, further comprising one or more additional components selected from the group consisting of an antioxidant, a stabiliser and a surfactant.

12. A nutraceutical composition comprising the lipid composition of claim 1.

13. A food product for human or animal consumption comprising the lipid composition of claim 1, wherein the DHA and the second and third polyunsaturated fatty acids are provided in the form of triglyceride esters.

14. The vegetable-based lipid composition of claim 1 for use in the treatment or prevention of cardiovascular disease, protection against death in patients with cardiovascular disease, reduction of overall serum cholesterol levels, reduction in high blood pressure, increase in HDL:LDL ratio, reduction of triglycerides, or reduction of apolipoprotein-B levels.

15. A method for producing the vegetable-based lipid composition of claim 1, comprising providing a mixture of fatty acid ethyl esters, and subjecting said mixture to a chromatographic separation process, optionally wherein the mixture of fatty acid ethyl esters is obtained by transesterification and distillation of a vegetable-based lipid oil.

16. The lipid composition of claim 4, wherein said C18-24 omega-3 polyunsaturated fatty acid containing at least three unsaturations is α-linolenic acid (18:3n-3), eicosatetraenoic acid (20:4n-3), docosapentaenoic acid (22:5n-3), or stearadonic acid (18:4n-3).

17. The lipid composition of claim 6, wherein said C18-24 omega-3 polyunsaturated fatty acid containing at least three unsaturations is α-linolenic acid (18:3n-3), eicosapentaenoic acid (20:5n-3), eicosatetraenoic acid (20:4n-3), docosapentaenoic acid (22:5n-3), or stearadonic acid (18:4n-3).

* * * * *